US008124404B2

(12) United States Patent
Alphey

(10) Patent No.: US 8,124,404 B2

(45) Date of Patent: Feb. 28, 2012

(54) STABLE INTEGRANDS

(75) Inventor: Luke Alphey, Abingdon (GB)

(73) Assignee: Oxitec Limited, Oxfordshire (GB)

( * ) Notice: Subject to any disclaimer, the term of this patent is extended or adjusted under 35 U.S.C. 154(b) by 1377 days.

(21) Appl. No.: 10/562,843

(22) PCT Filed: Jul. 1, 2004

(86) PCT No.: PCT/GB2004/002869

§ 371 (c)(1),
(2), (4) Date: May 15, 2006

(87) PCT Pub. No.: WO2005/003364

PCT Pub. Date: Jan. 13, 2005

(65) Prior Publication Data

US 2006/0212949 A1 Sep. 21, 2006

(30) Foreign Application Priority Data

Jul. 1, 2003 (GB) .................................. 0315379.8

(51) Int. Cl.
*C12N 15/00* (2006.01)

(52) U.S. Cl. ...................... 435/320.1; 435/462; 435/473

(58) Field of Classification Search ........................ None
See application file for complete search history.

(56) References Cited

U.S. PATENT DOCUMENTS

| | | | |
|---|---|---|---|
| 5,254,801 | A | 10/1993 | Dotson et al. |
| 5,851,796 | A | 12/1998 | Schatz |
| 6,200,800 | B1 | 3/2001 | Choulika et al. |
| 6,338,040 | B1 | 1/2002 | Buman et al. |
| 6,962,810 | B2 | 11/2005 | Fraser et al. |
| 2003/0150007 | A1 | 8/2003 | Savakis et al. |
| 2003/0213005 | A1 | 11/2003 | Alphey et al. |
| 2005/0221430 | A1 | 10/2005 | Prentice |
| 2006/0242717 | A1 | 10/2006 | Alphey |
| 2006/0275276 | A1 | 12/2006 | Alphey |
| 2007/0056051 | A1 | 3/2007 | Alphey |
| 2008/0115233 | A1 | 5/2008 | Alphey et al. |
| 2009/0183269 | A1 | 7/2009 | Alphey |

FOREIGN PATENT DOCUMENTS

| | | |
|---|---|---|
| EP | 0955364 | 11/1999 |
| GB | 2355459 | 4/2001 |
| WO | 98/08960 | 3/1998 |
| WO | 00/73510 | 12/2000 |
| WO | 01/39599 | 6/2001 |
| WO | 01/59088 | 8/2001 |
| WO | 01/91802 | 12/2001 |
| WO | 02/46444 | 6/2002 |
| WO | 02/101061 | 12/2002 |
| WO | WO 2004/044150 | 5/2004 |
| WO | 2004/098278 | 11/2004 |
| WO | 2005/003364 | 1/2005 |
| WO | 2005/012534 | 2/2005 |
| WO | 2007/091099 | 8/2007 |

OTHER PUBLICATIONS

Rong et al., Science vol. 288 (2000) pp. 2013-2018.*
Atkinson et al. (2000) "Hermes and Other hAT Elements as Gene Vectors in Insects," In; Insect Transgenesis: Methods and Applications, Hadler et al. eds., Boca Raton CRC Press, pp. 219-235.
Cabera et al. (2002) "Expression Pattern of Gal4 Enhancer Trap Insertions Into the bric à brac Locus Generated by P Element Replacement," Genesis 34:62-65.
Elick et al. (1997) "Analysis of the Cis-Acting DNA Elements Required for piggyback Transposable Element Excision," Mol. Gen. Genet. 255:605-610.
Gloor et al. (1991) "Targeted Gene Replacement in *Drosophila* Via P Element-Induced Gap Repair," Science 253:1110-1117.
Gonzy-Treboul et al. (1995) "Enhancer-Trap Targeting at the Broad-Complex Locus of *Drosophila melanogaster*," Genes Dev. 9:1137-1148.
Handler et al. (2001) "A Current Prospective on Insect Gene Transformation," Insect Biochem. Mol. Biol. 31(2):111-128.
Handler, A. (2002) "Use of piggyback Transposon for Germ-Line Transformation of Insects," Insect Biochem. Mol. Biol. 32:1211-1220.
Heslip et al. (1994) "Targeted Transposition at the vestigial Locus of *Drosophila melanogaster*," Genetics 138:1127-1135.
Horn et al. (2003) "piggyBac-Based Insertional Metagenesis and Enhancer Detection as a Tool for Functional Insect Genomics," Genetics 163(2):647-661.
Horn et al. (2002) "Fluorescent Transformation Markers for Insect Transgenesis," Insect Biochem. Mol. Biol. 32:1221-1235.
http://piggybac.bio.nd.edu/.
Johnson-Schlitz et al. (1993) "P-Element-Induced Interallelic Gene Conversion of Insertions and Deletions in *Drosophila melanogaster*," Mol Cell Biol. 13:7006-7018.
Lankenau et al. (1996) "Comparison of Targeted-Gene Replacement Frequencies in *Drosophila melanogaster* at the Forked and White Loci," Mol. Cell Biol. 16:3535-3544.
Rong et al. (2000) "Gene Targeting by Homologous Recombination in *Drosophila*," Science 288:2013-2018.
Rong et al. (2001) "A Targeted Gene Knockout in *Drosophila*," Genetics 157:1307-1312.
Russ et al. (1996) "Self-Deleting Retrovirus Vectors for Gene Therapy," J. Virol. 70:4927-4932.
Sepp et al. (1999) "Conversion of lacZ Enhanced Trap Lines to GAL4 Lines Using Targeted Transposition in *Drosophila melanogaster*," Genetics 151:1093-1101.
Steiner et al. (1995) "Homologous Recombination as the Main Mechanism for DNA Integration and Cause of Rearrangements in the Filamentous Ascomycete *Ashbya gossypii*," Genetics 140:973-987.
Wobus et al. (1990) "A New Transposable Element in *Chironomus thummi*," Mol. General Genet. 222:311-316.

(Continued)

*Primary Examiner* — Jim Ketter

(74) *Attorney, Agent, or Firm* — Greenlee Sullivan P.C.

(57) ABSTRACT

There is provided a transposable element comprising at least four inverted repeats, at least two of which are each inverted in relation to another, the element comprising DNA for insertion into a host genome, the DNA being located between two pairs of opposing repeats excisable by a transposase in situ to leave said DNA without flanking transposon-derived repeats in the host genome. Also provided is a transposable element comprising at least three inverted repeats, at least one of which is inverted in relation to the others, wherein at least one non-terminal repeat is a minimal repeat. Both these elements allow for greater efficiency of insertion of nucleotide sequences into the genome.

30 Claims, 10 Drawing Sheets

OTHER PUBLICATIONS

Prosecution history for related U.S. Appl. No. 10/148,041, 64 pp.
Prosecution history for related U.S. Appl. No. 10/556,804, 27 pp.
Prosecution history for related U.S. Appl. No. 10/566,448, 142 pp.
Prosecution history for related U.S. Appl. No. 11/352,177, 129 pp.
Prosecution history for related U.S. Appl. No. 11/733,737, 175 pp.
Prosecution history for related U.S. Appl. No. 12/278,849, 20 pp.
Examination Report for European patent application serial No. 04743590.4, dated Nov. 14, 2008, 4pp.
Search Report Corresponding to Great Britain Patent Application No. GB 0317656.7, Date of Search Nov. 25, 2003.
Search Report Corresponding to Great Britain Patent Application No. GB 0621234.4, Date of Search Feb. 21, 2007.
Search Report Corresponding to International Application No. PCT/GB2004/003263, Mailed May 11, 2004.
Search Report corresponding to International Application No. PCT/GB2007/000488, parent of the present application, (2007).
Written Opinion corresponding to International Application No. PCT/GB2007/000488, parent of the present application, (2007).
International Preliminary Report on Patentability, corresponding to International Application No. PCT/GB2007/000488, parent of the present application, (2007).
Alphey et al. (2002) "Dominant Lethality and Insect Population Control," *Mol. Biochem. Parasitol.* 121(2):173-178.
Alphey et al. (2007) "Managing Insecticide Resistance by Mass Release of Engineered Insects" J. Econ. Entomol. 100(5):1642-1649.
Arribas et al. (1986) "The ubiquitin genes in *D. melanogaster*: transcription and polymorphism" Biochimica et Biophysica Acta 868:119-127.
Bieschke et al. (1998) "Doxycycline-Induced Transgene Expression During *Drosophila* Development and Aging," Mol. Gen Genet. 258(6):571-579.
Blitvich et al. (2002) "Developmental- and tissue-specific expression of an inhibitor of apoptosis protein 1 homologue from *Aedes triseriatus* mosquitoes" Insect Molecular Biology 11(5):431-442.
Carriere and Tabashnik (2001) "Reversing Insect Adaptation to Transgenic Insecticidal Plants," *Proc. R. Soc. Lond. B*. 268:1475-1480.
Chen et al. (1996) "Apoptotic Activity of REAPER is Distict from Signaling by the Tumor Necrosis Factor Receptor 1 Death Domain" The Journal of Biological Chemistry 271(42):25735-25737.
Chen et al. (2000) "The Use of Modified Tetracycline Regulatory Expression System with Reduced Basal Level to Develop and In Vivo Biopesticide Expression System," Food Sci Agricult. Chem. 2(4):220-225.
Davis et al. (2001) "Engineered Underdominance Allows Efficient and Economical Introgression of Traits into Pest Populations," J. Theor. Biol. 212(1):83-98.
Ernst, U. (1991) "Regulation of Sexual Differentiation in *Drosophila*: Alternative Splicing of the *Transformer* Primary Transcript Requires Masking of the Non-Specific Acceptor Site in Females," Inaugural Dissertation, Aus Frankfurt / Main, BRD (Abstract Only).
Ernst, U. (1991) "Regulation of Sexual Differentiation in *Drosophila*: Alternative Splicing of the *Transformer* Primary Transcript Requires Masking of the Non-Specific Acceptor Site in Females," Inaugural Dissertation, Aus Frankfurt / Main, BRD.
Fu et al. (2007) "Female-specific insect lethality engineered using alternative splicing", Nature Biotechnology 25(3):353-357.
Funaguma et al. (2005) "The Bmdsx transgene including trimmed introns is sex-specifically spliced in tissues of the silkworm, *Bombyx mori*", Journal of Insect Science (online), 5(17):1-6.
Fussenegger et al. (1997) "Autoregulated Multicistronic Expression Vectors Provide One-Step Cloning of Regulated Product Gene Expression in Mammalian Cells" Biotechnol. Prog. 13:733-740.
Gong et al. (2005) "A dominant lethal genetic system for autocidal control of the Mediterranean fruitfly", Nature Biotechnology 23(4):453-456.
Gossen and Bujard (2001) "Tetracyclines in the control of gene expression in eukaryotes" Tetracyclines in Biology, Chemistry and Medicine, pp. 139-157.
Heinrich et al. (2000) "A Repressible Female-Specific Lethal Genetic System for Making Transgenic Insect Strains Suitable for a Sterile-Release Program," Proc. Nat. Acad. Sci. USA 97:8229-8232.
Hofmann et al.(1996) "Rapid Retroviral Delivery of Tetracycline-Inducible Genes in a Single Autoregulatory Cassette," Proc. Nat. Acad. Sci. USA 93:5185-5190.
Hondred et al. (1999) "Use of Ubiquitin Fusions to Augment Protein Expression in Transgenic Plants" Plant Physiology 119:713-723.
Horn et al. (2000) "Highly sensitive, fluorescent transformation marker for *Drosophila* transgenesis" Dev Genes Evol 210:623-629.
Horn et al. (2003) "A Transgene-Based Embryo-Specific Lethality System for Insect Pest Management," Nat. Biotechnol. 21(1):64-70.
Imai, C. (1987) "Control of Insecticide Resistance in a Field Population of Houseflies, *Musca domestica*, by Releasing Susceptible Flies," Res. Popul. Ecol. 29:129-146.
Louis et al. (2003) "A Theoretical Model for the Regulation of *Sex-Lethal*, a Gene That Controls Sex Determination and Dosage Compensation in *Drosophila melanogaster*," Genetics 165:1355-1384.
Loukeris et al. (1995) "Introduction of the transposable element *Minos* into the germ line of *Drosophila melanogaster*" Proc. Natl. Acad. Sci. USA 92:9485-9489.
Munoz et al. (2004) "The AeAct-4 gene is expressed in the developing flight muscles of female *Aedes aegypti*", Insect Molecular Biology 13(5):563-568.
Pane et al. (2002) "The *transformer* gene in *Ceratitis capitata* provides a genetic basis for selecting and remembering the sexual fate" Development 129:3715-3725.
Robinson et al. (2002) "Mutations and Their Use in Insect Control," Mutation Research 511(2):113-132.
Saccone et al. (2000) "Sex Determination in Medfly: A Molecular Approach," In; *Area-Wide Control of Fruit Flies and Other Pest Insects*, Tan, K.H. ed., Penerbit USM, Penag, pp. 491-496.
Saccone et al. (2002) "Sex determination in flies, fruitflies and butterflies" Genetica 116:15-23.
Scali et al. (2005) "Identification of sex-specific transcripts of the *Anopheles gambiae* doublesex gene", Journal of Experimental Biology 208(19):3701-3709.
Shelton et al. (2000) "Field Tests on Managing Resistance to *Bt*-Engineered Plants", Nature Biotechnology 18(3):339-342.
Shockett et al. (1995) "A Modified Tetracycline-Regulated System Provides Autoregulatory, Inducible Gene Expression in Cultured Cells and Transgenic Mice," Proc. Nat. Acad. Sci. USA 92:6522-6526.
Stebbins et al. (2001) "Tetracycline-Inducible Systems for *Drosophila," Proc. Nat. Acad. Sci. USA*. 98:10775-10780.
Stebbins et al. (2001) "Adaptable Doxycycline-Regulated Gene Expression Systems for *Drosophila*," Gene 270:103-111.
Thomas et al. (2000) "Insect Population Control Using Dominant, Repressible, Lethal Genetic System," Science 287:2474-2476.
Wool and Manheim (1980) "Genetically-Induced Susceptibility to Malathion in *Tribolium castaneum* Despite Selection for Resistance," Ent. Exp. & Appl. 28:183-190.
Wu et al. (2000) "Expression of Highly Controllable Genes in Insect Cells Using a Modified Tetracycline-Regulated Gene Expression System," J. Biotechnol. 80(1):75-83.

* cited by examiner 167161 gaaatcgattgcggaaaccattgcttagtttttgattgacctttgtttgaaaacaaaat
167221 atatgtataaaggaattatttgaaagtacgagcggtttgttgtcatattggtgggattt
167281 ttggctatttcattttaattaagtttttgaatttaaatgtttcatttagctacattca
167341 gaaatattgttttgaatttaaaaaatttacagtgtgaatgtcttgaatttttcaattgg
167401 aaaaaaaaggatgatggttgaagtatccgctttgtttattacagtagactggtcacact
167461 gccagctgctaaataatagaaaacagtctgcgtggacaaacatttaaTTAAaatgaatg
167521 taagcacttttaacgaaatctttgggaatatttcgctcatcagcattttatttgagca
167581 ggagtccgagtccccatcgacatacacacgctgaagctgcaggactggctgatcagccg
167641 cagaattgtgccaagaatgtgcagcaggagcttagggagatccacaggaagattagcaa

Figure 7

STABLE INTEGRANDS

CROSS REFERENCE TO RELATED APPLICATIONS

This is a National Stage application of PCT International Application No. PCT/GB2004/002869, filed on 1 Jul. 2004, which claims benefit of GB/0315379.8, filed 1 Jul. 2003, which is incorporated herein by reference in its entirety to the extent not inconsistent herewith.

The present invention relates to transposable elements and methods for their incorporation into the genome.

Transposable element technology has enabled the genetic transformation of a wide range of insects [cf. Handler, A. (2001), Insect Biochem Mol. Biol. 31, 111-128; Handler, A. (2002), Insect Biochem. Mol. Biol. 32, 1211-1220; Horn, et al., (2002), Insect Biochem. Mol. Biol. 32, 1221-1235], and at least some of these transposable elements have also been shown to be mobile over a much wider phylogenetic range, including prokaryotes and vertebrates (Handler, 2001, supra).

Transposons have been described extensively in the prior art. The elements used for genetic transformation of insects are generally characterised by opposing inverted repeat sequences and are associated with an optionally integral transposase enzyme. The transposase recognises the inverted repeat sequence and excises the sequences, together with any intervening DNA, and then reinserts the resulting transposon at another site, either in the genome or in a plasmid.

An autonomous transposon encodes its own transposase; for a type II transposon this is in the DNA between the inverted repeat sequences. Such autonomous transposons are not stably incorporated into the genome, as they are liable to move at random. Accordingly, where such a transposon is to be used to incorporate target DNA into a genome, it is preferred to provide the transposase on a helper plasmid, for example, so that transposition is dependent on the availability of the helper plasmid.

This system for incorporating genes or nucleic acid sequences into genomes is effective, but the transposed DNA is still associated with the inverted repeat sequences of the transposon, so that any future exposure to transposase can result in movement of the transposon, possibly even across the species barrier, although this unlikely.

The presence, or potential presence, of transposases capable of remobilising these insertions has led to objections to the use of this technology, particularly when the transformed organisms are for release into the environment. In addition, the presence of such transposases will tend to destabilise the insertions, which is generally undesirable. Though laboratory strains can be screened for the presence of related transposases by any of several methods, based, for example, on nucleic acid sequence similarity, such as by hybridisation or PCR, or function, such as plasmid-to-plasmid transposition assays or plasmid excision assays, it is not possible exhaustively to test all wild populations.

It is therefore desirable to develop transformation methods which lead to a transgenic line which is insensitive to transposase, or in which the insertion is insensitive to transposase.

In order to stabilise the genetic insert, it is possible to provide three or more repeats, and locate the insert between two repeats in the same orientation. It follows that the number of transposable elements is equivalent to the number of repeats in one orientation multiplied by the number of repeats having the opposite orientation. Exposing the construct to transposase will result in all of the possible transposable elements being obtained, including the entire length of the transposon containing the gene of interest, which can then be inserted into the genome. The resulting insertion can then lose the shorter length which does not contain the insert by further, or the same, transposase activity. This shorter length is a transposable element flanked by inverted repeats. Once removed, it leaves the desired genetic insert in place, but with only one repeat i.e. no longer within a functional transposable element, thereby disabling the ability of transposase to excise the genetic insert. This process is subject to extremely low success rates, however, as the transposase will usually generate the shortest length transposable element.

Thus, transposable elements with repeated ends can potentially utilise any of their repeated ends for transposition or excision. It is therefore possible to obtain transposition using a first distal end, followed by excision using another, more proximal end, leaving a fragment behind. This scheme is illustrated in FIG. 1.

In FIG. 1, triangles A-C represent the functional ends of the transposon, for example, the short inverted repeats at the ends of a class II element such as piggyBac. Transposition can occur between any two opposed triangles: in this case, A-B and A-C. Flanking transposon DNA may also be included, see below. An appropriate target site sequence, for example, TTAA or (A/T)N(A/T)TTAA(A/T)N(A/T) (SEQ ID NO:20) is also assumed to be included in these examples. Proximal and distal are relative to the 5' end. The construct of FIG. 1A is introduced into cells or embryos, for example, by microinjection, transfection, or ballistic or other methods, with a suitable transposase helper, for example, helper plasmid, RNA, transposase protein or integrated transposase source, also known as a jumpstarter.

A transformant containing the integrated product must then be selected, as shown in FIG. 1B.

The selected transformant is then exposed to a suitable source of active transposase, for example, helper plasmid, RNA, transposase protein or an integrated transposase source, to generate the specific excision product shown in FIG. 1C. The resulting product is substantially or completely stable to further exposure to active transposase, relative to the starting construct.

In the above example, two integration events are possible in the initial transformation step, then two excisions are possible once the desired integrant has been obtained. The alternative integration utilises the proximal 3' end, resulting in the insertion of a smaller transposon than desired, lacking the DNA of interest; the alternative excision utilises the distal 3' end, resulting in the complete excision of the construct and hence excision of the DNA of interest. Insect transformation is an inefficient process, so it is desirable to optimise the efficiency of this step. With suitable markers, even inefficient or rare excision may be acceptable, as an integrated transposase source can be used, so that it is possible to score large numbers of insects without requiring microinjection.

It is, therefore, highly desirable to maximise the efficiency of the first step, so as to provide the greatest possible number of initial transformants obtained by microinjection, for example, and obtain as many full-length insertions as possible and to maximise the ratio of full-length to short insertions.

The "3-end" system described above and illustrated in FIG. 1 has another weakness: the presence in the final product of a transposon end adjacent to the DNA of interest. In principle, insertion of another identical or cross-mobilising transposable element nearby could reconstitute a composite transposon and thereby destabilise the DNA of interest. There is, therefore, a need for a method to generate insertions in which no transposon ends remain.

Another available option for insect transformation involves adding another mobile element near or at one end of the transposon and rely on imprecise excision of this element to stabilise the insertion by deleting one end. This is an inherently unsatisfactory method as the nature of the deletion is unpredictable and uncontrollable.

Another method for generating transgenics without flanking transposon DNA is well known in *Drosophila*, though not for any other insect. This is the homologous recombination system of Rong and Golic (Rong, Y., and Golic, K. (2000), Science 288, 2013-2018; Rong, Y., and Golic, K. (2001), Genetics 157, 1307-1312). Essentially, the contents of a transposon insert are moved to another, predetermined chromosomal location. The new insertion need not have any transposon DNA, though it does have to have a target site for a site-specific recombinase, such as Flp/FRT. As originally described, this insertion is always associated with a large direct repeat. The main limitation of this scheme is the highly variable, and generally very low, rate at which the new homology-based insertions are recovered. It also requires several enzyme activities to be available, such as by prior establishment of transgenic lines, for example FLP and I-SceI. The main use of this system is to generate knock-outs or other targeted modifications to specific genes or sequences.

Various attempts in the art have been made to improve the effectiveness of transposition. WO 02/46444 discloses a transposable polynucleotide suitable for use in methods for manipulating nucleic acids to create libraries of cells containing transposed nucleic acid, wherein the transposable polynucleotide comprises two or more inverted repeat sequence pairs. Each pair has a distinct and separable ability to interact with a distinct transposase enzyme. The pairs can, for instance, be provided in a nested fashion such that both members of one pair are flanked by both members of the second pair. For instance, the Tn5 transposon, described therein, includes "inside end" sequences and "outside end" sequences. A transposase is disclosed that preferentially binds and interacts with the outside ends but not the inside ends.

WO 01/91802 discloses a chimeric nucleic acid vector comprising adenoviral inverted terminal repeat flanking regions comprising, between the inverted terminal repeats, retroviral long terminal repeat flanking regions, within which is further found a cassette comprising the DNA of interest and a gag nucleic acid region. Such vectors are capable of transducing all cis and trans components of a retroviral vector for the generation of a high tighter recombinant retroviral vector for use in in vivo gene transfer applications.

Wobus et al, Molecular and General Genetics, 1990, vol. 222, pp 311-316 describes a new transposable element from *Chironomus thummi* which is shown to have inverted repeats of 17 base pairs at each termini. The transposable element is called TECth1, is 1.7 kb long and was found in the 3' flaking region of a *C. thummi* Balbiani ring gene.

US 2002/0173634 sets out to solve problems in the use of the piggyBac vector caused by lack of suitable restriction sites to cut the components needed for gene transfer, and limitations on the sizes of genes transferred by use of this vector. This is achieved by removing large portions of apparently non-essential DNA from the piggyBac transformation vector.

U.S. Pat. No. 6,200,800 B 1 discloses retroviral vectors containing cis-acting viral elements from the expression, encapsidation, reverse transcription and integration of the retroviral genome nucleic acid sequence. A retroviral vector is provided for eliminating most of the viral elements which are not useful in the integrated provirus. The vector provided use, among other thing, the bacteriophage P1 Cre-lox recombination system.

Russ et al., J. Virology, 1996, vol. 70, pp. 4927-4932 discloses self-deleting retrovirus vectors for use in gene therapy. Russ et al. discloses how retrovirus vectors containing a loxP site fuse to independently expressed selectable marker generates proviruses flanked by loxP. This enables the Cre recombinase to excise most of the provirus apart from the marker gene.

Steiner S. et al., Genetics, 1995, vol. 140, pp. 973-987 shows that homologous recombination is the main mechanism for DNA integration and the cause of rearrangements in the filamentous ascomycete *Ashbya gossypii*.

What is required is a simple system with enhanced rates of initial transformation with a desired gene or nucleotide sequence.

Thus, according to a first aspect, the present invention provides a transposable element comprising at least four inverted repeats, forming at least two pairs of opposing pairs of inverted repeats, the element comprising DNA for insertion into a host genome, the DNA being located between two pairs of opposing repeats such that excision by a transposase or transposases of said pairs, in situ, is effective to be able to leave said DNA integrated into the host genome, without the presence of flanking transposon-derived repeats derived from said transposable element.

The DNA for insertion into a host genome is preferably a gene that is to be expressed in the host, although it is envisaged that it could preferably also be a genetic element that does not encode a protein, such as regulatory element, for instance a promoter or enhancer sequence.

Alternatively, it is also preferred that the DNA for insertion into a host genome is simply a DNA sequence for insertion into a target sequence for the purposes of, for instance, altering the frame of a coding sequence, disrupting the function of a gene or even deleting a portion of DNA if, for instance, the transposition occurs between target sites some distance apart.

A gene's function may be disrupted, for instance, by insertion of stop codon into the coding sequence thereof, insertion of suitable nucleotides sufficient to bring about a stop codon where one was not previously found in frame, or insertion of "junk" DNA into the coding sequence or untranslated regions, thereby disrupting the gene's promoter or enhancer, for instance.

Preferably, the inverted repeats are "piggyBac" repeats.

It is also preferred, the number of inverted repeats is 6, 7, 8 or more, but more preferably and most preferably 4, as transposases generally favour shorter sequences to transpose or excise, thus making it preferable to have as few inverted repeats as possible to minimise unwanted transpositions and excisions and to promote the intended transpositions and excisions. This is so as to, for instance, leave only the gene-of-interest remaining in the host genome, such that as much as possible of the genetic material derived from the transposon, with the exception of the gene-of-interest, is removed.

Whilst it is preferred to remove only some of the transposon-derived DNA from the host genome, such as only one excisable transposon of opposing inverted repeats, it is more preferable to excise all transposon-derived DNA from the host genome, apart from the gene or DNA of interest.

The inverted repeats, also referred to as "ends" in the art, are preferably homologous, such that the repeat sequence is the same, albeit inverted. This has the advantage of requiring only one transposase. Alternatively, it is also preferred that the different pairs of homologous repeats are heterologous, such that they do not form opposing inverted repeats which may be transposable or excisable. Preferably, the heterologous repeats are recognised by different transposases, thereby allowing the user to exert control over different transposition and excision steps.

The transposase is preferably autonomous, such that the transposase is encoded within the transposon itself. However, it is also preferred that the transposase is provided by another means, such as a further genetic element comprising the transposase, for instance another transposon or preferably a helper plasmid, thereby also allowing the user a greater level of control as to when the various stages of the transposition and excision according to the present invention occur.

The transformant is preferably exposed to a suitable source of active transposase, for example, a helper plasmid or RNA encoding the transposase, or a transposase protein or integrated transposase source, as known in the art.

Preferably, one or more of the inverted repeats is a minimal repeat, as discussed below. In this instance, it is preferred that the minimal repeat is non-terminal, i.e. it is an internal repeat, as discussed below.

It is also preferred that markers are associated with the transposon in order to allow the user to follow the progress of the various steps of transposition and excision and to determine in which individuals have been said steps have successful. Suitable markers and systems therefor are also discussed below. Preferably at least one genetic marker is associated with an identifiable step in the transposition/excision process, and more preferably, the marker is associated with the DNA for insertion into a host genome.

Preferably, the DNA for insertion into a host genome does not comprise any inverted repeats or target sites for insertion of the present invention, which could lead to unwanted excision of part or all of a previous insertion, or to the transposable element of the present invention being transposed into a previous insertion. Although it may be impractical to have absolutely no inverted repeats or insertion sequences in the DNA for insertion into a host genome, it is preferred that these be kept to a minimum or that they are heterologous to, and therefore not recognised by, the transposase or transposases used by the present invention.

Opposing inverted repeats are capable of recognition by a suitable transposase, leading to transposition or excision of the repeat and intervening DNA. If the inverted repeats are not opposing, i.e. they are orientated in such a way that the second repeat sequence is not a complementary mirror image of the first repeat sequence, then no transposition or excision will occur between these repeats. This can be seen in FIG. 1A, where repeats A and B are opposing, thereby allowing transposition/excision therebetween, whereas repeats B and C are not opposing. It can also be seen in FIG. 3A, where the two repeats marked 5' are not opposing, nor is the left hand 3' repeat in relation to the right hand 3' repeat. In the diagrammatic representations used in FIGS. 1-4, an opposing pair of repeats is shown by a 5' arrow and a 3' arrow pointing in opposite directions.

The opposing inverted repeats of the present invention are preferably excised in situ, from the host genome, following initial transposition of the full-length element, comprising the at least four repeats and the DNA of interest, into the host genome.

Preferably, the element comprises two external opposed inverted repeats, one on each side of an inversion cassette, the cassette comprising;

the DNA for insertion into a host genome, two inverted cassette repeats and two inversion sites, the DNA for insertion into a host genome being flanked on either side by one of the inverted cassette repeats, each inverted cassette repeat being further flanked by an inversion site;

the cassette being capable of inversion within the transposed element in situ in the presence of a recombinase, such that following inversion, the two inverted cassette repeats flanking the DNA for insertion into a host genome each separately form a further pair of opposing inverted repeats with one of the external inverted repeats, the further pairs of opposing repeats being excisable by a transposase in situ to leave said DNA without flanking transposon-derived repeats in the host genome.

It will, of course, be appreciated that the repeats or inversion sites that, for instance, are said to be flanking or bounding another feature, are not necessarily intended to be directly adjacent thereto, but may be proximal or have a spacer therebetween, provided that this does not impair the function of either feature. In some cases, it is envisaged that such a spacer may be useful and may even include a marker, for instance.

The external inverter repeats are found on each side of the inversion cassette. Before inversion, the external opposing repeats form a pair of opposing inverted repeats transposable by a transposase, such that the repeats and the cassette comprised therebetween are transposed into the host genome by the transposase. Following inversion of the cassette in the host genome by a recombinase, each of the external repeats then forms a new excisable element or transposon with an opposing inverted repeat that is now opposing as a result of the inversion. Two further newly-formed opposing pairs of inverted repeats are found, one on each side of the inverted cassette and are excisable. Being shorter than the pair formed between the two external repeats found at either end of the transposed and inverted element and comprising the DNA or gene of interest, the newly-formed repeats are favoured over the longer repeat and are excisable in preference thereto, leaving only the DNA of interest, preferably with minimal flanking sequences, in the host genome.

A transposon-derived repeat is a repeat that originated in the transposable element and not from the host genome, or is homologous to, complementary to or a variant of that original repeat.

The inversion sites are sequences recognised by inversion-inducing recombinase. Preferably, such sites comprise the Flp or Cre sites from the Flp/FRT or Cre/lox inversion systems, or any other such systems known in the art. Preferably, the inversion sites are recognised by a directional recombinase, the recombinase-mediated inversion being essentially irreversible. Preferred sites of this type are, for instance, lox66 or lox71.

The inversion cassette preferably comprises the DNA of interest, the two inverted cassette repeats which later go on to form one half of the opposing repeats that are used to excise the transposon-derived DNA, and the inversion sites, such as the FRT site of a Flp/FRT system or a lox site from a Cre/lox system, which direct the recombinase to the inversion of the intervening DNA. Preferably, the cassette may also comprise markers, as discussed below.

The present invention also provides a method of transposition comprising use of the transposable element to insert DNA of interest into a host genome, together with the transformant or organisms produced by said method.

In one aspect the present invention preferably provides a transposable element comprising at least four inverted repeats, at least two of which are inverted in relation to the others, comprising DNA for insertion into a host genome located between two pairs of opposing repeats excisable by a transposase in situ to leave said DNA without flanking transposon-derived repeats in the host genome.

Inverted repeats are sequences which are found in identical (but inverted) forms. In other words, the repeats have the same sequence running in the 5' to 3' direction, except that these sequences are on different strands of the DNA. For example, 5'-CCCTAG-3' and 5'-CTAGGG-3' are inverted repeats as the second sequence is the mirror image of the first, except that the mirror image has also been converted into the antisense of the first, such that A has been converted to T, C to G and so forth. Thus, the complementary sequence of the second repeat reads 3'-GATCCC-5' (5'-CCCTAG-3'), the same of the first repeat, only on the complementary strand.

The inverted repeat sequences of piggyBac transposons, for example, are associated with short, external TTAA sequences, which generally correspond to the insertion site. It is, therefore, preferred that such sequences are provided with the terminal inverted repeats of the present invention.

FIG. 3 illustrates a scheme involving two pairs of inverted repeats flanking the gene or DNA of interest, and how this may be used to generate an insert ultimately associated with no transposon repeats.

The construct of FIG. 3A is injected with a suitable transposase helper, for example, helper plasmid, RNA, transposase protein or integrated transposase source.

A transformant containing an integrated product as shown in FIG. 3B may then be selected, and exposed to a suitable source of active transposase, for example, helper plasmid, RNA, transposase protein or integrated transposase source.

Transformants containing either of the specific excision products shown in FIG. 3C may then be selected. Further exposure to transposase may then be employed to obtain the final excision product shown in FIG. 3D.

As mentioned above, the inverted repeat sequences of piggyBac transposons, for example, are associated with short, external TTAA sequences, which generally correspond to the insertion site. The inverted repeats are also associated with internal stretches of DNA. These internal stretches of DNA can be deleted to leave a minimal repeat, so that the repeats simply flank the desired DNA to be inserted. Transposons created in this manner are capable of excision and plasmid-to-plasmid transposition, and can do so with frequencies similar to those of constructs containing more internal piggyBac sequence (Elick et al., 1997, supra). However, such minimal piggyBac elements are not capable of efficient germline transformation, giving transposition frequencies approximately 20× lower than more complete elements.

It has also recently been established that transposable activity is retained if part of the repeat is deleted, but that the resulting insert can no longer be excised by transposase activity at the truncated repeat.

It has now been found that it is possible to provide a transposon with three or more inverted repeats of which a middle repeat is a minimal repeat, such a transposon providing significantly enhanced levels of initial transformation.

Thus, in a further aspect, the present invention provides a transposable element comprising at least three inverted repeats, at least one of which is inverted in relation to the others, wherein at least one non-terminal repeat is a minimal repeat.

Preferably, the element comprises DNA for insertion into a host genome located between the minimal repeat and a repeat having the same orientation as the minimal repeat.

The DNA for insertion into a host genome is preferably flanked by two pairs of opposing repeats excisable by a transposase in situ to leave said DNA without flanking repeats in the host genome, although it preferred that each of the repeats bounding the DNA for insertion into a host genome is a minimal repeat.

It is preferred that at least one repeat distal to the DNA for insertion into a host genome in relation to a minimal repeat in the same orientation has an internal deletion or is otherwise compromised over up to 50% of its length, thereby reducing the frequency of excision by a transposase at that repeat.

Preferably, at least one genetic marker associated with an identifiable step in the transposition/excision process and more preferably, the marker is associated with the DNA for insertion into a host genome.

It will be appreciated the greatest length of a transposon is the distance between, and including, the two opposing repeats farthest from each other. Other, shorter transposons can then be defined within the length of the longest transposon by the presence of other repeats. It is at least one of these non-terminal, or internal, repeats that are preferably minimal repeats.

As used herein, the term 'minimal repeat' applies to the highly conserved repeat sequences observed to be required for the activity of a given transposase. The piggyBac transposon, for example, has a 32 bp terminal inverted repeat interrupted by a 4 bp insertion at the 5' end and a 31 bp insertion at the 3' end. This can be considered as two pairs of inverted repeats, one of 13 bp and another of 19 bp, these two being separated by 4 bp at the 5' end and 31 bp at the 3' end. The minimal repeat, in this instance, then comprises a 32 bp repeat with a 4 or 31 bp insertion at the 5' and 3' ends respectively.

It is generally preferred to provide the flanking sequences commonly associated with the terminal repeats. In the case of piggyBac, this is preferably TTAA.

In general, transposases will be more effective at cutting out shorter sequences so that, where a transposon has one 5' repeat and two 3' repeats, for example, the most common transposon that will be observed transferring to another locus will be the shorter, formed by the 5' repeat together with the more proximal of the two 3' repeats. This preference is both inevitable, owing to the fact that the longer transposon will still be cut by the transposase, as well as being exacerbated by topological considerations, whereby repeats in closer proximity appear to be bound substantially better by transposases.

The present invention overcomes this problem by employing at least one minimal repeat internal to the longest transposon of the construct. This minimal repeat is utilised at only very low rates for the original insertion, thereby strongly biasing the initial reaction to generating the larger transposon. Any DNA of interest is located between the minimal repeat and a corresponding full length repeat in the same orientation.

WO 0/0441504 discloses the use of a 3 end (3 inverted approach), but there is no mention of the use of minimal ends. There is a discussion of the use of inversion, similar to that used in conjunction with the transposable element comprising at least 4 inverted repeats according to the first aspect of the present invention. However, WO 0/0441504 only discloses the use of inversion in relation to the 3 end approach and not in relation to a 4 end approach.

It will be appreciated that minimal repeats may simply comprise the minimum repeat necessary to effect transposition, and be associated with none of the original intervening DNA between the repeats observed in piggyBac, for example. However, the present invention envisages using some of the internal sequence, although it is preferred to keep this to a minimum, as greater lengths will increase the transposition frequency of the minimal repeat, thereby diminishing the desirable bias discussed above. Accordingly, while it is preferred to keep internal sequence associated with the minimal repeat to zero nucleotides, it is possible to use up to 100 bases, for example, of the original sequence, but it is preferred to use 50, or less, and preferably 10 or less.

Correspondingly, for the full length sequences, there is no clearly established limit as to what constitutes full length. It is established, however, that between about 6 and 14% of the internal sequence of a naturally occurring transposon is sufficient to provide high levels of transposition frequency, so that the present invention generally prefers that 'full length repeat sequences' be associated with at least 5% of the original internal sequence of the transposon from which they are derived, with between 6% and 14% being preferred, and 8% to 12% being more preferred.

The transposons of the present invention may employ two or more minimal repeats, although two is the preferred maximum. Where two are used, then it is preferred that these both be internal and in opposite orientations. Where two smaller transposons flank the DNA of interest, this has the particular advantage of encouraging the full length transposable element to be incorporated into the genome and then losing the two smaller transposons, thereby leaving simply the DNA of interest without any flanking repeats. This method is also provided herein, simply using full length repeats, as defined above.

It is preferred to use a minimal piggyBac end as the more proximal of the distal ends and a fully-functional piggyBac end as the distal end. This arrangement strongly biases the initial transformation step towards insertion of the desired longer transposon.

In an alternative embodiment, multiple copies of the 3' and/or 5' ends is provided, with minimal repeats preferably providing the inmost of any series of repeats in the same orientation. This increases the chance that one or more longer versions of the transposon are integrated in the initial transformation, as required. One version of this is illustrated diagrammatically in FIG. 2.

The construct of FIG. 2A is introduced into cells or embryos, for example, by microinjection, transfection, or ballistic or other methods, with a suitable transposase helper, for example, helper plasmid, RNA, transposase protein or an integrated transposase source.

A transformant containing the integrated product of FIG. 2B is then selected, and exposed to a suitable source of active transposase, for example, helper plasmid, RNA, transposase protein or integrated transposase source. Transformants containing the desired specific excision product, as shown in FIG. 2C, can then be selected.

While efficiency in the second, excision step is less critical, as large numbers of individuals can readily be screened, it is preferred that the excision preferentially removes the short transposon, rather than a long one, as frequently as possible. The present invention provides such a system. piggyBac elements with suitable deletions or mutations in their internal inverted repeat are competent for transposition but not for excision, or have reduced excision rates. Use of such a modified end as the distal end will therefore bias the excision reaction towards utilisation of the proximal end as a higher proportion of the total of excision events.

Thus, it is preferred to use, as a terminal repeat, a repeat having a deletion of no more than 50%, or mutation or inversion that disables no more than 50% of the repeat. It is preferred that such a compromised repeat be in the same orientation as the minimal repeat, where there is only one. These repeats are readily transposed, but are not readily excised after transposition, thereby biasing the excision reaction towards the minimal repeat. Where more than one minimal repeat is used, in opposing orientations, then more than one compromised repeat may also be used.

The compromised repeat is generally preferred to correspond to a full length repeat, other than in respect of the deletion or mutation.

In relation to either aspect of the present invention, it is possible that subsequent exposure to transposase will simply lead to excision of the entire sequence, in which case the organism is effectively unaltered from the original. The alternative provides the DNA of interest in combination with one full length repeat, but no corresponding inverted repeat, so that the insert is no longer part of a transposable element.

It will also be appreciated that the sequences with which the repeats are associated need not correspond completely to the original sequences found in the naturally occurring transposons, and that variation and sequence degeneracy are encompassed within the scope of the present invention. In particular, it is preferred that any original sequence associated with the repeats of the present invention have at least 70% homology with the corresponding natural sequence, more preferably at least 80%, more preferably at least 90%, and particularly 95% or above, especially 100%.

In order to ensure that the resulting organism has been transformed in the manner desired, it is preferred to utilise appropriate markers. These may be used in any manner suitable to inform the skilled person as to the status of the transformant. For example, markers may be associated with the DNA of interest in order to demonstrate that the organism has successfully been transformed. Markers may be incorporated in the areas between repeats that are to be deleted, so that the initial transformant containing the full length sequence can be detected. Any suitable combination of markers may also be used.

It is generally preferred that markers be selectable, either positive or negative, and suitable examples are illustrated hereinunder.

The use of any transposable element is envisaged, but class II elements, such as Hermes, hobo, Minos, and mariner, are preferred, owing to their relatively high fidelity during transposition, and the piggyBac element, which is known to use the distal element of a repeated pair at relatively high frequency [Elick, et al., (1997), Mol. Gen. Genet. 255, 605-610], is particularly preferred.

Suitable transposable elements will be known to the skilled person and although reference is made to piggy Bac elements in several examples of the present invention, it will be appreciated that the present invention is not limited thereto and that such reference was made purely for the purpose of exemplification of he invention.

The present invention also provides a method of creating a new marker, preferably by a rearrangement such as that discussed below. Furthermore, the present invention also extends to a method of removing a conditional lethal. If one or both of the flanking transposons contained a conditional lethal gene, one could use this as a negative selection for the original element, and thereby select the desired excision product, even if quite rare. This is equivalent to the use of visible markers, but simpler and requires less effort, so that more transformants can be screened.

The present invention has been shown to work in insects as these are useful and well understood models for genetic transposition. However, it will be appreciated that the present invention will also be useful in a whole range of organisms for transposition into a DNA genome. Accordingly, the present invention is useful in mammals, but also in plants, fungi, and even prokaryotes and viruses.

The present invention, therefore, also provides a method for transforming an organism, comprising exposing replicative cells or tissue of the organism to an element according to the present invention under conditions effective to incorporate the element into the genome thereof and, subsequently or simultaneously therewith, providing conditions suitable to excise a transposon from the genome, and selecting an organism, or cells or tissue therefor, comprising the DNA intended for insertion lacking repeats in at least one orientation. Preferably, the organism is a mammal, a plant, a fungus, a prokaryote, such as bacteria or a virus.

The present invention also encompasses an organism obtained in accordance with the transposable element and method discussed herein. Preferably the organism is an insect.

The final transgenic line preferably has no transposon DNA whatsoever associated with the insertion, unless this has been deliberately incorporated into the DNA of interest. Since there is no known upper or lower limit for the length of transposition-competent piggyBac elements that would constrain the length of the DNA of interest, the present invention provides a method of very general utility for inserting DNA into genomes of cells or organisms. However, we generally prefer that the total length of the initial piggyBac transposon be in the range 3-25 kb, as this corresponds approximately to the range of piggyBac transposons commonly used for germline transformation in insects.

There is no lower limit to the amount of DNA that can be inserted by the overall procedure, after the flanking transposons have been excised. The initial insertion will retain the target site specificity of the original element, such as TTAA for piggyBac, with some apparent preference for (A/T)N(A/T)TTAA(A/T)N(A/T) (SEQ ID NO:20), which may also be written as WNWTTAAWNW (SEQ ID NO. 20) where "W" denotes A or T. Precise excision of the elements will resolve this to a duplication of the TTAA, flanking the DNA of interest, which can be as short as a single nucleotide. In the event that zero nucleotides are inserted, only the TTAA duplication remains. The insertion of larger fragments is generally preferred.

A suitable example of a small insertion is a stop codon. Insertional mutagenesis using transposable elements is a well known method for genetic screens of various types. However, interpreting the phenotype may be complicated by the presence of the transposon, with its associated markers, promoters and other elements. A short insertion, such as TTAA or CTAG, which provides a total sequence between the piggyBac ends of TTAATTAATTAA (SEQ ID NO. 1) and TTAACTAGTTAA (SEQ ID NO. 2), respectively, allows the insertion to be resolved to a TTAA duplication with this four base insertion. TTAATTAATTAA (SEQ ID NO. 1) and TTAACTAGTTAA (SEQ ID NO. 2), in these examples, provide stop codons in all three frames in both directions. An insert of zero base pairs provides a frame shift and a stop codon in two frames, although one of these is already present in the original TTAA.

The present invention may be used to provide a coding region, such as for a fluorescent protein or a transactivator protein, such as GAL4, GAL4delta, or tTA. An insertional mutant may then be resolved to a fusion protein. As this needs to be in frame and in the correct orientation to function, it is generally preferable to also provide a suitable IRES (internal ribosome entry site) element and coding region, to allow bicistronic expression, or two such in opposite directions to allow bicistronic expression for insertions of either orientation.

The present invention may also be used to insert an enhancer or promoter or a suitable target site for a site-specific recombinase, either with or without a marker and other sequences. Initial experiments with the non-deleted transposon may serve to establish the presence or absence of specific enhancer effects on a particular insertion site, and the viability and other properties of individuals carrying large insertions at this site. Suitable insertions could then be resolved by stepwise excision to the recombinase target site, either with or without a marker and other sequences. This could then be used as a docking site to enable the insertion of other DNA sequences at this pre-determined and partially pre-characterised position. This arrangement has significant benefits in allowing the insertion of heterologous DNA at a predetermined site. If desired, the site can be protected from nearby enhancers by flanking the recombinase target site with suitable insulator elements, for example scs and scs', or HS4.

The present invention may also be used to replace an existing transposon insertion with specific DNA in such a way that the insertion is substantially or completely stable to further exposure to active transposase. This can be performed by replacing the existing transposon with a composite transposon of the present invention. Methods for performing such a replacement have been described [cf. Johnson-Schlitz, et al., *Mol Cell Biol* 13, 7006-18 (1993); Cabrera, et al., *Genesis* 34, 62-5 (2002); Sepp, et al., *Genetics* 151, 1093-101 (1999); Lankenau, et al., *Mol Cell Biol* 16, 3535-44 (1996); Gonzy-Treboul, et al., *Genes Dev* 9, 1137-48 (1995); Heslip, et al., *Genetics* 138, 1127-35 (1994); Gloor, et al., *Science* 253, 1110-7 (1991)].

Minimal molecular markers are generally characteristic of one aspect of the invention. It will be apparent to the person skilled in the art that PCR-based or other molecular analysis is capable of distinguishing each of the various possible forms at each stage.

However, with respect to both aspects of the invention, it is generally more convenient to provide at least one visible or selectable marker, and this is preferred. Suitable markers are well known to the person skilled in the art, and include: genes encoding fluorescent proteins, including GFP, DsRed and their mutant derivatives; genes encoding drug or antibiotic resistance, such as neomycin phosphotransferase, or hygromycin resistance; and markers capable of functionally complementing a visible mutant in the host organism, such as mini-white$^+$ or rosy$^+$ in *Drosophila*, white$^+$ in *Ceratitis capitata* or *Drosophila* cinnabar complementing kw$^w$ in *Aedes aegypti*. It is particularly preferred that at least one such marker be associated with the section of DNA containing the DNA of interest, allowing the segment to be tracked through the integration and stepwise excision process.

Where the DNA of interest segment is associated with two repeated ends, then each of the two flanking elements may be marked. Double selection may be used to recognise the initial insertion and then track the stepwise excisions. Since the last step has no high-probability alternatives, individuals with the DNA of interest can be recovered in the final step even though they no longer have any associated visible marker. Thus, the present invention provides a novel method for recovering transgenics with no selectable marker.

Visible markers can generally be scored for or against, in other words are generally suitable for either positive or negative selection. Automated, or semi-automated systems for identifying, or identifying and separating individuals are available, and have the potential for screening very large numbers of individuals, for example in the transformation or excision steps. For the excision step, negative selection for the appropriate transposon is desirable, together with positive selection for the DNA of interest, or an associated marker, as appropriate for the precise scheme selected. Negative selection markers are also known that can be used to select against particular individuals carrying them; such a system can be conveniently used to screen, or to help to screen large numbers of individuals for excision of a specific region. Suitable negative selection markers include inducible or repressible lethals, one half of a biphasic expression system such as GAL4/UAS or tTA/tRE, if the other half can be provided separately, dominant temperature sensitive lethals such as the *Drosophila* DTSs, or synthetic ones such as a suitable toxic element operably linked to a heat-shock or other inducible or repressible promoter.

Multiple visible markers can be provided not only by using mutant derivatives of fluorescent proteins, for example, of GFP and DsRed, which are independently distinguishable based on their spectral properties (c.f. Horn et al., 2002, supra), but alternatively by expressing the same or similar markers in different spatial or temporal patterns. For example, it is readily possible to distinguish between *Drosophila* Act5C-DsRed, which shows ubiquitous expression, particularly clear in the body of larvae and in the adult eye, and Act88F-DsRed, which shows in indirect flight muscles only, and is, therefore, visible in the thorax of late pupae and adults. These markers are, therefore, separated by both their spatial and their temporal patterns and insects carrying one, the other, or both can readily be distinguished.

Where the present invention relates to transposable elements with two repeated ends, though the initial transformation reaction and the first excision reaction have several potential outcomes, of which not all are desirable, the second excision reaction has only one excision product, and this is the desired one. Accordingly, it is possible not to mark one of the flanking transposons, to select by suitable methods the desired products of the first two reactions, and then to conduct the second excision reaction blind, by exposure to transposase, for example, at high concentration, or for several generations of exposure to a jumpstarter element, then identify the desired reaction product by molecular methods. It is also possible to perform both excision reactions in this way, selecting only for the presence of a marker in the intervening sequence. It is, therefore, possible to perform the entire sequence of reactions using only a marker in this region. This embodiment provides for particularly short flanking transposons, and thus for the maximum size of insert for a given initial composite transposon size.

It will be appreciated that though each step of the insertion sequence is described separately, in practice, exposure to transposase may induce several of these steps to occur within one generation, or without the intermediate being specifically identified. This is generally acceptable and may provide a faster route to the desired final structure, and may be encouraged or stimulated by the use of relatively high concentrations of transposase, or the use of hyperactive transposase or cis-acting sequences, if desired. It will be understood that suitable use of molecular and/or selectable markers can facilitate this process.

Transposases are necessary to the function of the present invention, but it is not critical as to how they are provided. They may be provided in any suitable manner, as detailed below, and may be inherent in the cell, provided on plasmids or even provided within the element itself, although this is not preferred. The cell may also be dosed with the enzyme or mRNA encoding the enzyme, or even with a virus expressing the enzyme, for example.

Suitable transposase can be provided in any of several forms: injection or electroporation, for example, of a plasmid or RNA encoding the transposase, or of transposase protein itself. A transposase source may also be integrated into the target genome, to provide a 'jumpstarter' construct, or line. This is a preferred method for the excision steps; the jumpstarter element can be combined with the initial insertion by conventional breeding, or by making the primary transformant in the jumpstarter line. Excision products will then be generated spontaneously, without requiring further injection or electroporation. With suitable markers or molecular analysis, the desired products can readily be isolated, and separated from the jumpstarter, if required, by conventional breeding.

Although jumpstarters provided within the transposons of the invention are not generally preferred, it is possible to provide a coding sequence therefor in a shorter internal transposon that it is desired to excise. Thus, it is possible to generate a jumpstarter line through insertion of an autonomous element, followed by its resolution by self-catalysed excision.

Transposition is thought to work by a number of mechanisms. One such mechanism involves "scanning" by the transposase. In this mechanism, the transposase binds to one repeat, probably a specific repeat, and scans along the DNA looking for the other repeat. This scanning may or may not be directional. However, where more than one repeat can be recognised by the transposase, as shown for instance in FIG. 2, the nearer of two duplicated repeats will be used much more frequently than the other repeat.

This would not appear to be the case for piggybac, which is, therefore, thought not to use such a scanning mechanism, but probably is the case for other class II transposons.

Therefore, in order to enhance the rate of transposition of the full length element comprising the gene of interest, minimal ends may be used, as described above, or an internal rearrangement of the element after insertion can be induced.

The rearrangement or inversion approach starts with a plasmid with only two functional transposable elements, where one transposable element includes the DNA of interest, whereas the other uses the "internal" ends and excludes the DNA of interest, see FIG. 3A. After transposition into the genome and recombinase-induced rearrangement/inversion, the initial transposon is converted into a sequence comprising the gene-of-interest and two flanking transposable elements, together with a longer transposable element comprising all three, see FIG. 3B. However, under the scanning mechanism, the two shorter flanking transposable elements should then be much more readily mobilised, leaving only the gene-of-interest and one (FIG. 3C), but preferably neither (FIG. 3D), of the flanking elements remaining.

Inversion is when a chromosomal segment is excised and reinserted in the same place but turned 180 degrees from its original orientation, so that the gene sequence for the segment is reversed with respect to that of the rest of the chromosome.

Suitable systems for such an inversion are well known in the art, such as Cre/10× and Flp/Frt recombinase systems. The cre recombinase is a product of lambda phage in *Escherichia coli*, and the FLP recombinase is an enzyme native to the 2 micron plasmid of *Saccharomyces cerevisiae*. These recombinases alter the arrangement of DNA sequences in very specific ways. The FLP recombinase, for instance, is active at a particular 34 base pair DNA sequence, termed the FRT (FLP recombinase target) sequence. When two of these FRT sites are present, the FLP enzyme creates double-stranded breaks in the DNA strands, exchanges the ends of the first FRT with those of the second target sequence, and then reattaches the exchanged strands. This process leads to inversion or deletion of the DNA which lies between the two sites. Whether there is an inversion or deletion depends on the orientation of the FRT sites: if the sites are in the same direction, the intervening DNA will be deleted, but if the sites are in opposite orientation, the DNA is inverted.

Recombination using wild-type 10× or FRT sites is reversible. However, the use of directional recombinase sites, e.g.

mutants of lox such as lox66 and lox71, which will recombine with each other in an essentially irreversible reaction, is also envisaged, and generally preferred as these will prevent re-inversion whereby the inversion cassette is subjected to a second round of inversion, such that it is returned to its original orientation. Therefore, the use of directional recombinases biases the inversion to give only the desired product. Other recombinases, whose wild type targets are non-identical and have an essentially irreversible reaction, are also known, e.g. phage C31 integrase acting on attP and attB sites.

Therefore, it is envisaged that the element comprises two external opposed inverted repeats bounding an inversion cassette. The cassette comprises the DNA for insertion into a host genome, together with two inverted repeats and two inversion sites. The DNA for insertion into a host genome is flanked on either side by one of the inverted repeats, each inverted repeat being further flanked by an inversion site, such that reading 5'-3' along one strand of DNA in the cassette, there is provided an inversion site such as FRT, a first inverted repeat, the gene or other DNA of interest, followed by a second inverted repeat and finally by the second inversion site.

The cassette is capable of inversion within the transposed element in situ, in the presence of a recombinase. Once the full length transposon has been transposed into the host genome, the recombinase induces inversion of the DNA between the inversion sites.

The result of this is that that following inversion, the two inverted repeats, flanking the DNA of interest, each separately form a new pair of opposing inverted repeats. They do so with one of the external inverted repeats, thus forming a new pair of opposing repeats that are being excisable by a transposase in situ, thus leaving the DNA of interest without flanking transposon-derived repeats in the host genome.

The inversion sites, are preferably suitably orientated with respect to each other to allow inversion rather than deletion of the DNA therebetween. For instance, with the Flp/FRT system commonly known to in the art and used here as a non-limiting example only, are preferably aligned in opposite orientations to allow inversion rather than deletion.

The inversion sites are preferably suitably orientated with respect to each other to allow inversion rather than deletion of the DNA therebetween, As with the transposase the recombinase may, preferably, be encoded by the transposable element of the present invention or, even more preferably, separately therefrom.

Clearly, this recombinase-based inversion approach requires an additional step. The efficiency of this step could be increased by using mutant recombinase target sequences, which make the reaction essentially irreversible. A good marker system would also be useful to detect such rearrangements and is provided in accordance with the invention. Here, for instance, the recombinase target sites are embedded in two different markers, such that following rearrangement, two new markers are created.

For example, marker 1 might be EGFP under the control of an eye-specific promoter; marker 2 might be DsRed under the control of a ubiquitous or body-specific promoter. The recombinase target site is included in each marker between the promoter and the coding region for the fluorescent protein. The initial transgenic then exhibits green fluorescent eyes and red fluorescent body, while individuals carrying the desired recombination product (which is an inversion of an internal section of the composite transposon) show red fluorescent eyes and a green fluorescent body. Individuals carrying the desired inversion should therefore be readily detected, even if rare.

Accordingly, the present invention also provides a method of creating a new marker by such a rearrangement, such as the red eyes produced in the above example. Furthermore, the present invention also extends to a method of removing a conditional lethal.

Without being bound by theory, it is worth noting that the 31 base pair spacer found in the right hand (3') piggyBac repeat may wrap around a protein, in contrast to the 3 or 4 base pair spacer in the 5' repeat, perhaps suggesting that the transposon is an evolutionary ancestor of the VDJ antibody variation domain of the MHC, where a similar mechanism is also seen.

EXPERIMENT 1

Use of Minimal Ends

We made construct pLA1025 (see FIG. 5 and SEQ ID NO. 3), which includes minimal piggyBac ends (35 bp and 63 bp bases for 5' and 3' respectively). We generated transgenic *Drosophila melanogaster* carrying this construct by co-injection with a helper plasmid into a white-eyed strain (Handler and James 2000; Handler 2002, below). Potential transgenics were screened for fluorescence characteristic of EGFP and DsRed. pLA1025 contains 4 potential transposons, marked with [Actin5C-EGFP, Actin5C-DsRed2 and Actin88F-DsRed2], [Actin5C-EGFP and Actin88F-DsRed2 but not Actin5C-DsRed2], [Actin5C-EGFP only] and [Actin88F-DsRed2 only], respectively.

If all transposon ends were utilised with equal efficiency, one might expect these 4 transposons to be recovered with equal frequency, or possibly a higher frequency for the shorter transposons which contain only one marker. Of 5 independent transgenic lines recovered from 85 G0 adult injection survivors, all showed all three markers, and therefore correspond to the desired composite transposon. This indicates that the utilisation of ends and nature of the recovered transposons can be biased in a desirable way by using internal ends that are less readily utilised for plasmid-to-germline transposition.

A diagrammatic representation of the pLA1025 construct is shown in FIG. 5 and its predicted sequence given in SEQ ID NO. 3.

EXPERIMENT 2

Resolution of Four-End Constructs to Give Transgenic Strains in which DNA of Interest is No Longer Flanked by Transposon DNA We made construct pLA1125 which includes 4 piggyBac ends, two each of 5' and 3' ends. pLA1125 is shown diagrammatically in FIG. 6 and its predicted sequence is shown in (SEQ ID NO. 4)

We generated transgenic *Drosophila melanogaster* carrying this construct by co-injection with a helper plasmid into a white-eyed strain (Handler and James 2000; Handler 2002, below). Potential transgenics were screened for fluorescence characteristic of DsRed. We recovered transgenics in the progeny of 12 out of 227 adult G0 injection survivors. PCR analysis for the presence of each of regions 1, 2 and 3, and their contiguous presence, showed that all these transgenic lines contained a composite transposon of the expected structure.

This demonstrated that, although pLA1125 contains 4 potential transposons, transgenics containing the desired composite transposon (PB5'-ZsGreen-PB3'-DsRed2-PB5'-AmCyan-PB3') could be recovered at a useful rate. We found that neither ZsGreen nor AmCyan could be reliably scored by fluorescence microscopy in these transgenic flies, despite the presence of the coding regions for these proteins as analysed by PCR, so subsequent experiments used fluorescence microscopy as a reliable determinant of the presence of DsRed only. Parallel experiments with other constructs indicated that the OpIE2 promoter fragment used to drive expression of ZsGreen and AmCyan in LA1125 gives only weak expression in *Drosophila*, furthermore the AmCyan region of LA1125 contains a frameshift likely to reduce or eliminate production of functional AmCyan protein.

One of these transgenic LA1125 lines (line 12) was selected for further study. We determined the insertion site by obtaining flanking DNA and sequencing, then comparing this sequence with the known genomic DNA sequence of *Drosophila melanogaster* from the *Drosophila* genome project. This showed that the composite LA1125 element had inserted into the sequence located on chromosome 2. This is shown in FIG. 7 where the site of insertion is written in capital letters and underlined, and in (SEQ ID NO. 5).

We exposed the integrated LA1125 line 12 (henceforth "1125-12") to piggyBac transposase by crossing to piggyBac "jumpstarter" lines, either pCasper-hs-orf (see the piggybac.bio website), or pHer {3×P3-ECFP, hsp70-piggyBac} (Horn, N et al. 2003). Progeny of these crosses were heatshocked during embryonic and larval development (37° C. for 1 hr, 2× per week, starting 0-7 days after egg deposition, at which point parents were removed, stopping when first pupae were observed in vial). Double heterozygous (1125-12/+ and jumpstarter/+) F1 adults were selected, based on marker expression.

Somatic Transposition

Extracts from pools of 5 double heterozygous (1125-12/+ and jumpstarter/+) adults, or from individual flies, were analysed for excision of the flanking simple transposons by PCR, see Tables 1 and 2 below. Precise excision of either element would bring the flanking genomic DNA closer to the central DsRed gene. This would lead to a characteristic, predictable, reduction in size of a PCR product using Dro-12m$^{-4}$+su-a5c-r1 primers or Dro-12m-1+Diag-droso primers for PCR, respectively detecting excision of the ZsGreen or AmCyan simple transposon.

TABLE 1

| Primer's name | Predicted size of PCR product from 1125-12 | Predicted size of PCR product from 1125-12 following deletion of ZsGreen simple transposon |
|---|---|---|
| Dro-12m-4 + su-a5c-r1 | 3058 bp | 277 bp |

TABLE 2

| Primers | Predicted size of PCR product from 1125-12 | Predicted size of PCR product from 1125-12 following deletion of AmCyan simple transposon |
|---|---|---|
| Dro-12m-1 + Diag-droso | 2913 bp | 268 bp |

In all pools and all individuals analysed, we observed the characteristic bands expected for precise excision of each simple transposon (FIG. 8). We did not observe such bands from similar extracts of flies from the 1125-12 line which had not been exposed to transposase. We therefore conclude that it is possible to eliminate each of the two flanking transposons from the composite 1125 transposon, while retaining the central region. We further conclude that this excision is substantially dependent on the presence of piggyBac transposase, as expected. Since the PCR band is of the expected size for a precise excision, and piggyBac excisions are known to be precise in the large majority of cases, we conclude that precise somatic excision of the flanking elements is occurring at a readily detectable rate.

FIG. 8 shows the PCR detection of somatic excision of the flanking transposons in F1 adults flies after exposure to transposase, wherein:

M=DNA marker (SmartLadder, Eurogentec)

A=PCR for the excision of ZsGreen simple transposon

B=PCR for the excision of AmCyan simple transposon

A1 and B1=template DNA from a pool of 5 F1 flies which were exposed to transposase A2 and B2=template DNA from a single F1 fly which was exposed to transposase A3 and B3=template DNA from a single fly which had no exposure to transposase Germ-Line Transposition In order to determine whether the flanking transposons could be eliminated in the germ-line, to generate gametes containing the excision products and hence a heritable excision product, double heterozygous (1125-12/+ and jumpstarter/+) F1 adults were crossed to white-eyed ($w^{1118}$) flies. Pools of 7 F2 progeny flies, selected for the presence of the DsRed marker by fluorescence microscopy, were obtained. Extracts from these pools were analysed for the presence of the specific excision products as above. Several pools yielded specific PCR bands as for the somatic excision assay above. One example is shown in FIG. 9. This indicates that germline excision can occur as for somatic excision above.

FIG. 9 shows the PCR detection of germline excision of ZsGreen simple transposon, wherein:

M=DNA marker (SmartLadder, Eurogentec)

1-7=DNA extracted from different pools of 7 F2 1125-12 flies (with DsRed)

Dro-12m-4 and su-a5c-r1 primers were used in these PCR reactions 192 individual flies were analysed for excision by using the primers which had been used to detect the somatic and the germline excision of ZsGreen and Amcyan simple transposons. These flies were also analyised for the presence of ZsGreen (su-zsgreen-f+su-zsgreen-r) and Amcyan (su-amcyan-f+su-amcyan-r) simple transposons and for connections between the central DsRed region with ZsGreen (Diag-rab-b-g+su-a5c-r1) and with AmCyan (Opie2-nhe-R+Diag-droso) simple transposons.

The somatic excision data, and the data from pools of F2 individuals, clearly indicates that precise excision of the flanking transposons can occur. However, in a careful PCR-based analysis of four of the individual F2 flies showing excision events, we were unable to amplify a diagnostic flanking DNA band of the type used to show precise excision in somatic cells. However, these flies had clearly lost one or both of their flanking transposons, as judged by the inability to amplify unique regions from one or both of these transposons (primers su-zsgreen-f and su-zsgreen-r for the ZsGreen transposon and su-amcyan-f and su-ancyan-r for the AmCyan transposon), while being readily able to amplify a unique region from the central DsRed region (primers su-red-f and su-red-r) and indeed to observe fluorescence characteristic of DsRed in these flies.

We conclude that the excision event that removed the flanking simple transposons was associated with a rearrangement, possibly a deletion of flanking genomic DNA but, more likely, a transposition of the composite transposon such that it is no longer associated with the original flanking DNA but is now inserted at a new site in the genome. The ability to recover remobilised, products of this type is an advantage, as it indicates that an initial primary transformant can be simultaneously relocated to another site and stabilised by elimination of one or both flanking transposons, which saves a considerable amount of time over the multi-generational breeding scheme that would be required to obtain such a product if each step had to be performed sequentially.

We further analysed the two DsRed-positive flies in which neither ZsGreen nor AmCyan appeared to be present. PCR using primers PB5-sh-srf-asc-1 and PB5-sh-not-hind-2, which amplify a section of piggyBac, showed that no such piggyBac DNA is present anywhere in these flies (FIG. 10). The ZsGreen and AmCyan transposons have not, therefore, rearranged or transposed to another part of the genomes of these flies, rather they have been completely lost, presumably by excision in the germ-line of the F1 parent. We have therefore demonstrated that it is possible by this method to generate transgenic flies in which the inserted DNA is not associated with the ends of a transposon.

FIG. 10 shows the results of PCR analysis of piggyBac sequence in DsRed stable transformants, wherein:

M=DNA marker (SmartLadder, Eurogentec)

1=DNA from LA1125-12 flies unexposed to transoposase used as positive control

2=DNA from fly 70 (has neither ZsGreen nor AmCyan)

3=DNA from fly 200 (has neither ZsGreen nor AmCyan)

Markers

The ZsGreen and AmCyan open reading frames were used only as molecular markers in these experiments. Use of visible markers would reduce the amount of PCR required, as phenotypic scoring for the presence of such markers, e.g. for the production of fluorescent proteins, could be used to infer excision and other events. However, we have clearly demonstrated that this is not necessary, that these events occur at sufficient frequency that molecular-based screening alone is sufficient to recover the desired types, e.g. excision products. Two variants of LA1125 are therefore proposed based on the above data: (i) an equivalent construct with visible markers in the flanking transposons and (ii) an equivalent construct with shorter flanking transposons containing no such visible markers. The second of these options should give higher transposition and excision frequencies, as shorter transposons are generally thought to be more active. A short segment of unique sequence in each of the flanking transposons would be helpful for the molecular analysis. Such a construct is also the product of a Flp/Frt, Cre/10× or other similar inversion system following recombinase-mediated inversion of the central section of the construct described.

Vector pLA1125 provides several unique sequences into which additional DNA could be inserted. Particularly convenient in this regard are the AscI and SrfI sites in the central section. pLA1125, and the variants described above, therefore provide vectors of general utility for the method of the invention.

Primers

Primers are given below in Table 3

TABLE 3

| Primer Name | Sequence |
|---|---|
| Dro-12m-1 | gccagtcctgcagcttcagcgtgtg (SEQ ID NO. 6) |
| Dro-12m-4 | aaaggtatgatggttgaagtatccgc (SEQ ID NO. 7) |
| Diag-droso | ccttctttgttgaatccagatcctgc (SEQ ID NO. 8) |
| Diag-Ra-b-g | gctcctgggcaacgtgctggttg (SEQ ID NO. 9) |
| Opie2-nhe-R | ggtggctagcttgcgcttcttcttgggtgggg (SEQ ID NO. 10) |
| PB5-sh-srf-asc-1 | ggtgggcgcgcccaattgcccgggctttttaaccctagaaagatagtctgcgt (SEQ ID NO. 11) |
| PB5-sh-not-hind-2 | gcccaagcttgcggccgcgtcattttgactcacgcggtcg (SEQ ID NO. 12) |
| su-a5c-r1 | gatttgattcagagttgatgccattcatg (SEQ ID NO. 13) |
| su-amcyan-f | ccagacctccaccttcaaggtgacc (SEQ ID NO. 14) |
| su-amcyan-r | ttgtaggaggtgtggaactggcatctg (SEQ ID NO. 15) |
| su-red-f | caacaccgtgaagctgaaggtgacc (SEQ ID NO. 16) |
| su-red-r | cttggccatgtagatggacttgaactcc (SEQ ID NO. 17) |
| su-zsgreen-f | caagcaggccatcaacctgtgc (SEQ ID NO. 18) |
| su-zsgreen-r | gacttggccttgtacacggtgtcg (SEQ ID NO. 19) |

REFERENCES FOR EXPERIMENTS 1 AND 2

Handler, A. (2002). "Use of the piggyBac transposon for germ-line transformation of insects." Insect Biochem. Mol. Biol. 32: 1211-20.

Handler, A. and A. James (2000). Insect transgenesis: methods and applications. Boca Raton, CRC Press.

Horn, C., O. N, et al. (2003). "piggyBac-based insertional mutagenesis and enhancer detection as a tool for functional insect genomics." Genetics 162(2): 647-661.

BRIEF DESCRIPTION OF THE FIGURES

FIG. 1A shows a transposon construct with opposing transposon repeats A and B proximal (5') to DNA of interest, and repeat C, not opposing repeat B, distal (3') to the DNA of interest. FIG. 1B shows the transposon construct of FIG. 1A integrated into genomic DNA. FIG. 1C shows the integrated construct of FIG. 1B after excision of the proximal transposon sequences.

FIG. 2A shows the transposon construct with transposon sequences flanking DNA of interest. FIG. 2B shows the transposon construct of FIG. 2A integrated into genomic DNA. FIG. 2C shows the integrated transposon construct of FIG. 2A after excision of distal transposon sequences or after excision of proximal transposon sequences. FIG. 2D shows the integrated DNA of interest after excision of both proximal and distal transposon sequences.

FIG. 3A shows the transposon construct with recombinase sites oriented in opposite directions indicated by large open arrows. FIG. 3B shows the transposon construct integrated into genomic DNA, and the construct after inversion of the DNA of interest with suitable recombinase. FIG. 3C shows the integrated construct after excision of the distal and/or the proximal sequences, and FIG. 3D shows the integrated DNA of interest flanked only by genomic DNA.

FIG. 4A shows a transposon construct having a single 5' transposon end and several 3' ends, all opposed to the 5' end. One of these is proximal to the 5' end, relative to the DNA of interest, whereas the others are distal. FIG. 4B shows possibilities for integration of this construct in forms that include integration of the DNA of interest with loss of no distal repeats, loss of the outermost distal repeat, and loss of the two outermost distal repeats. FIG. 4C shows the integrated construct after excision of the proximal transposon sequences.

FIG. 7 shows a DNA sequence (SEQ ID NO:5) of *Drosophila melanogaster* DNA showing the insertion site (capitalized and underlined) of a composite LA1125 element into a sequence located on chromosome 2.

SEQUENCE LISTING

Figure 1:
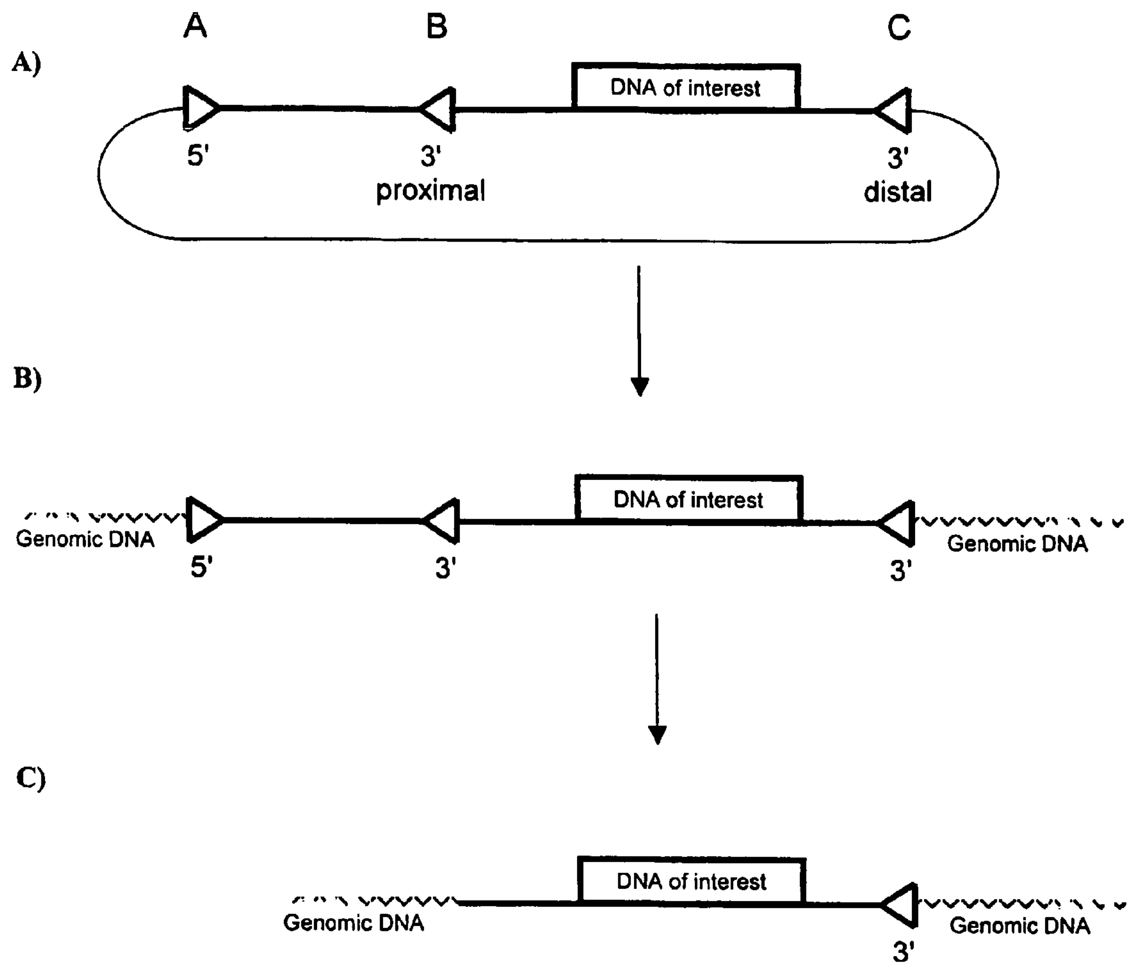
FIG. 1 illustrates a transposition scheme wherein triangles A-C represent the functional ends of the transposon. Opposing repeats are shown by 5' and 3' arrows pointing in opposite directions.
Figure 2:
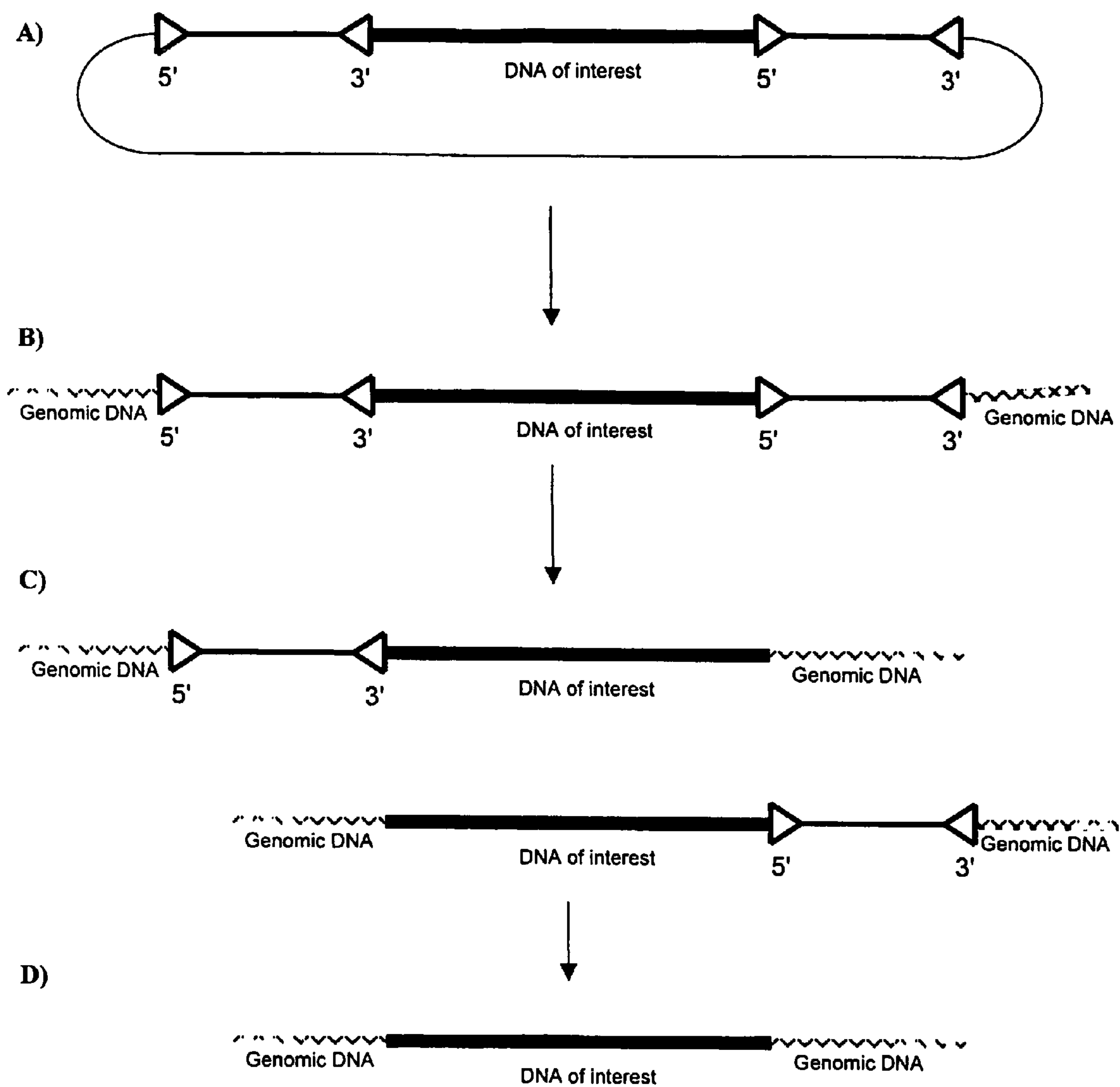
FIG. 2 illustrates an embodiment of a transposition scheme using a transposon construct.
Figure 3:
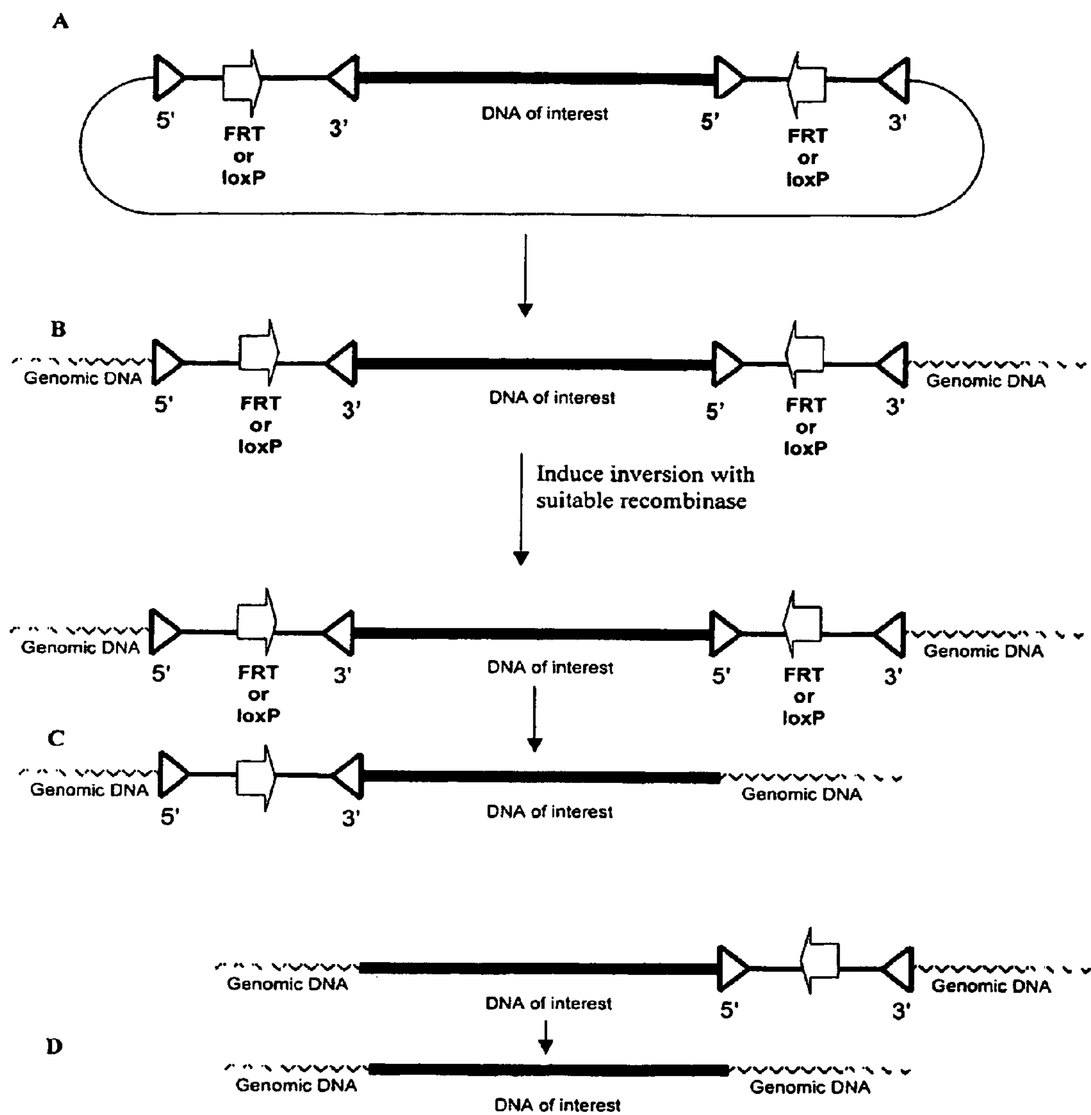
FIG. 3 illustrates a scheme involving two pairs of inverted repeats flanking the gene or DNA of interest.
Figure 4:
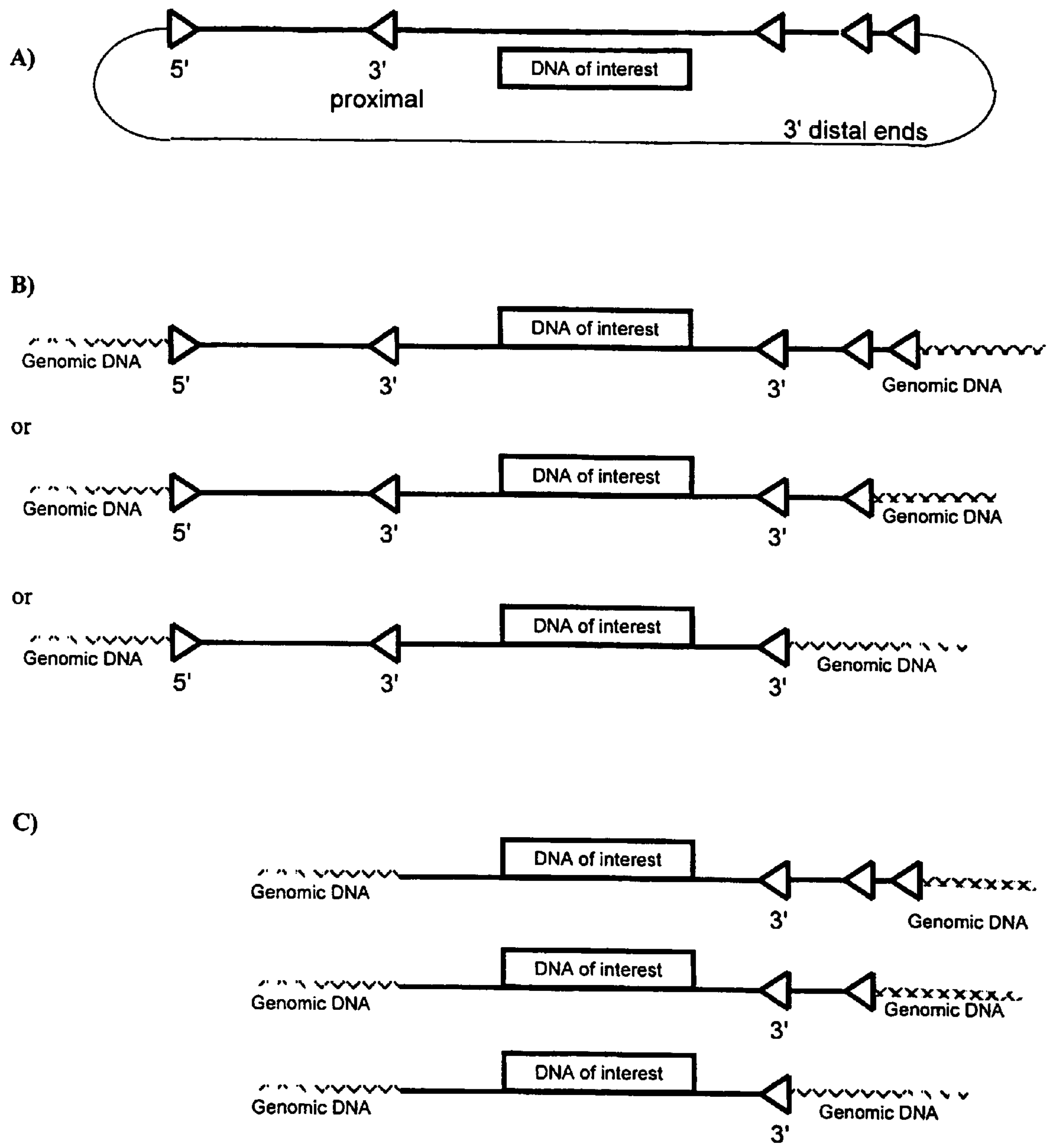
FIG. 4 shows further transposition schemes.
Figure 5:
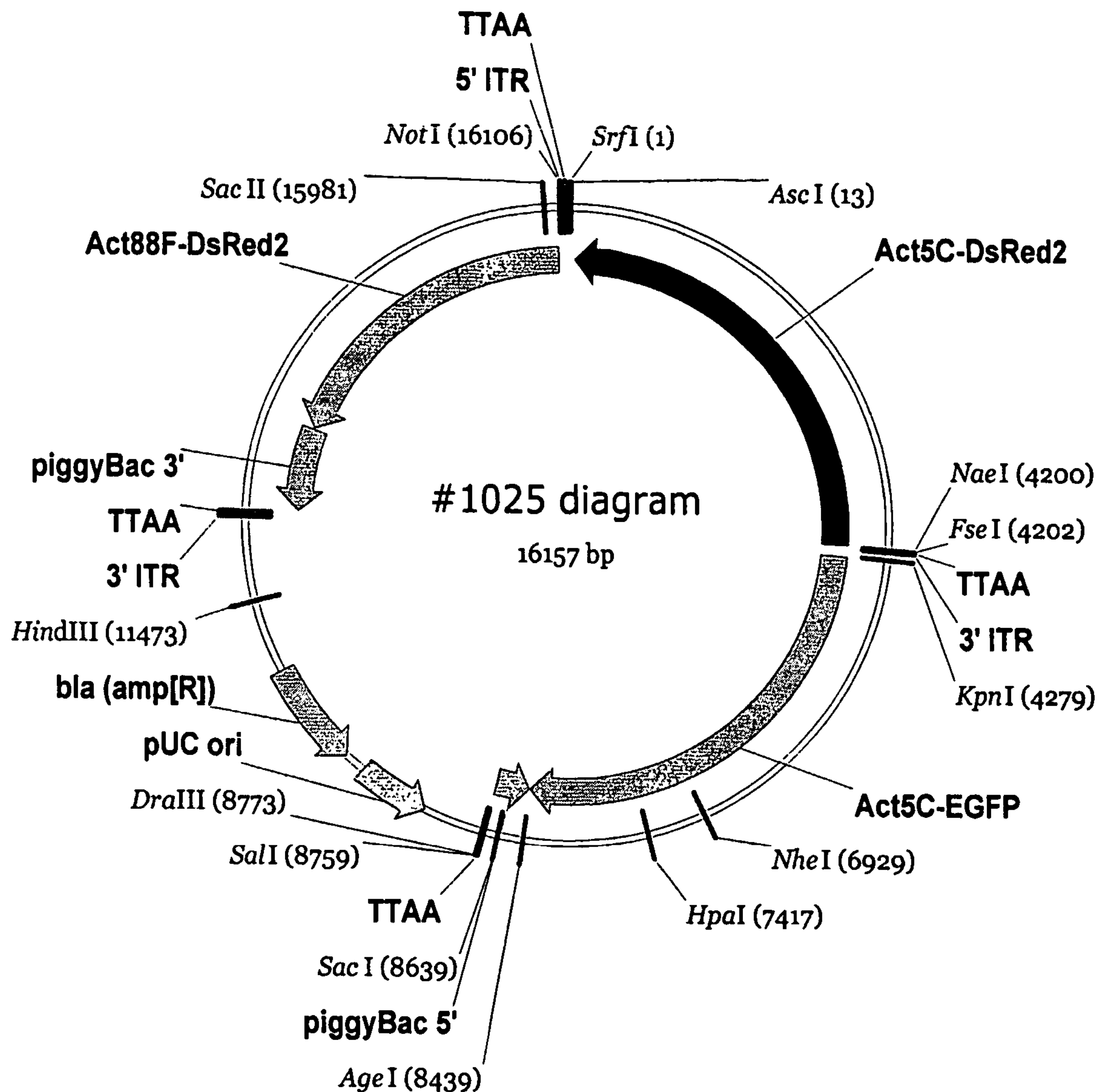
FIG. 5 shows a diagrammatic representation of the pLA1025 plasmid construct.
Figure 6:
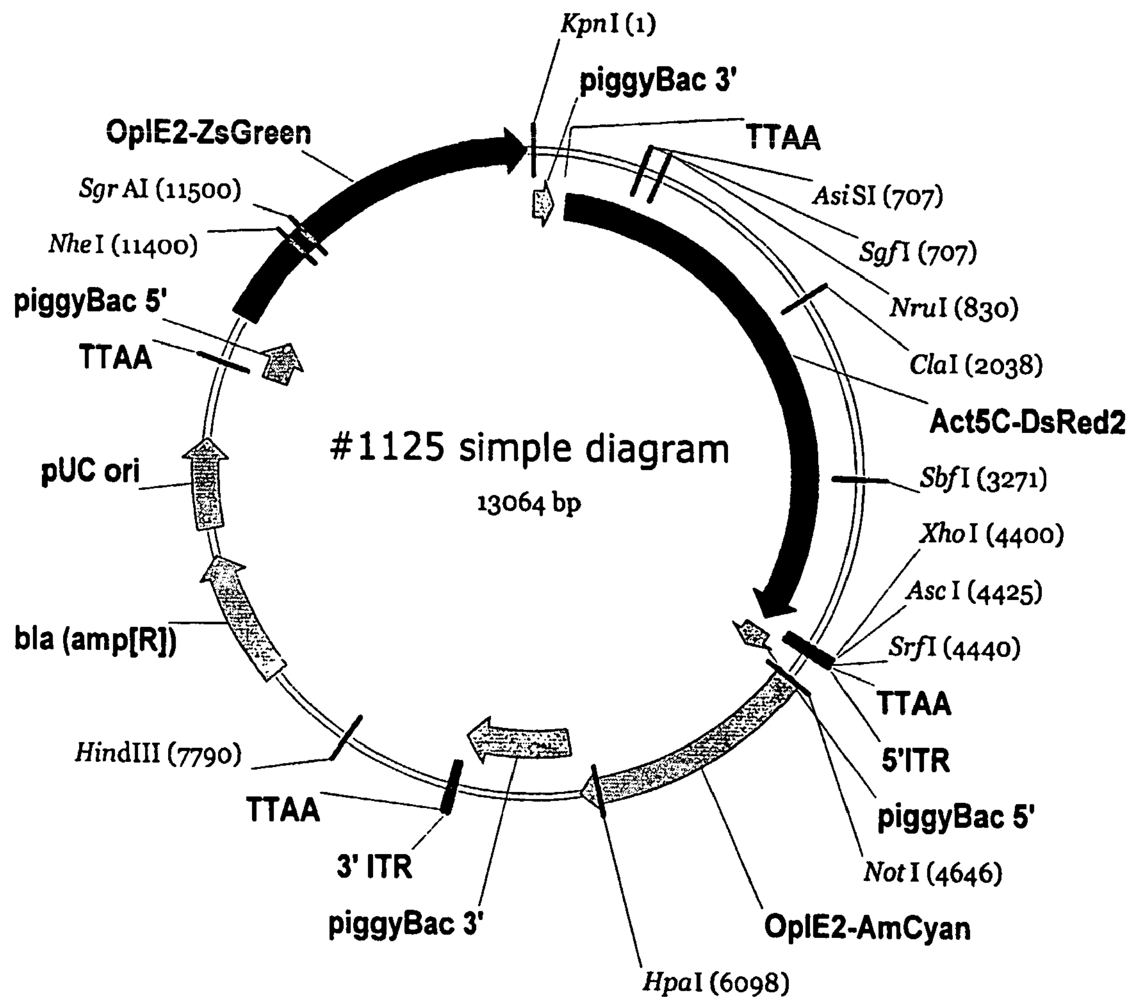
FIG. 6 shows a diagrammatic representation of the pLA1125 plasmid construct.
Figure 8:
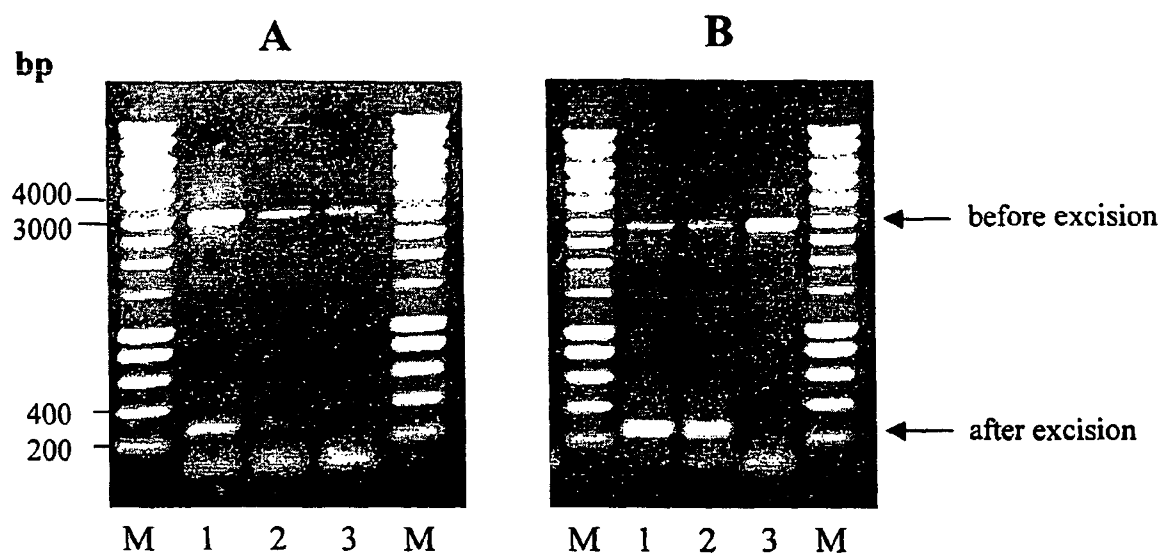
FIG. 8 shows PCR detection of somatic excision of the flanking transposons in F1 adults flies after exposure to transposase, wherein: M=DNA marker (SmartLadder, Eurogentec); A=PCR for the excision of ZsGreen simple transposon; B=PCR for the excision of AmCyan simple transposon; A1 and B1=template DNA from a pool of 5 F1 flies which were exposed to transposase; A2 and B2=template DNA from a single F1 fly which was exposed to transposase; and A3 and B3=template DNA from a single fly which had no exposure to transposase.
Figure 9:
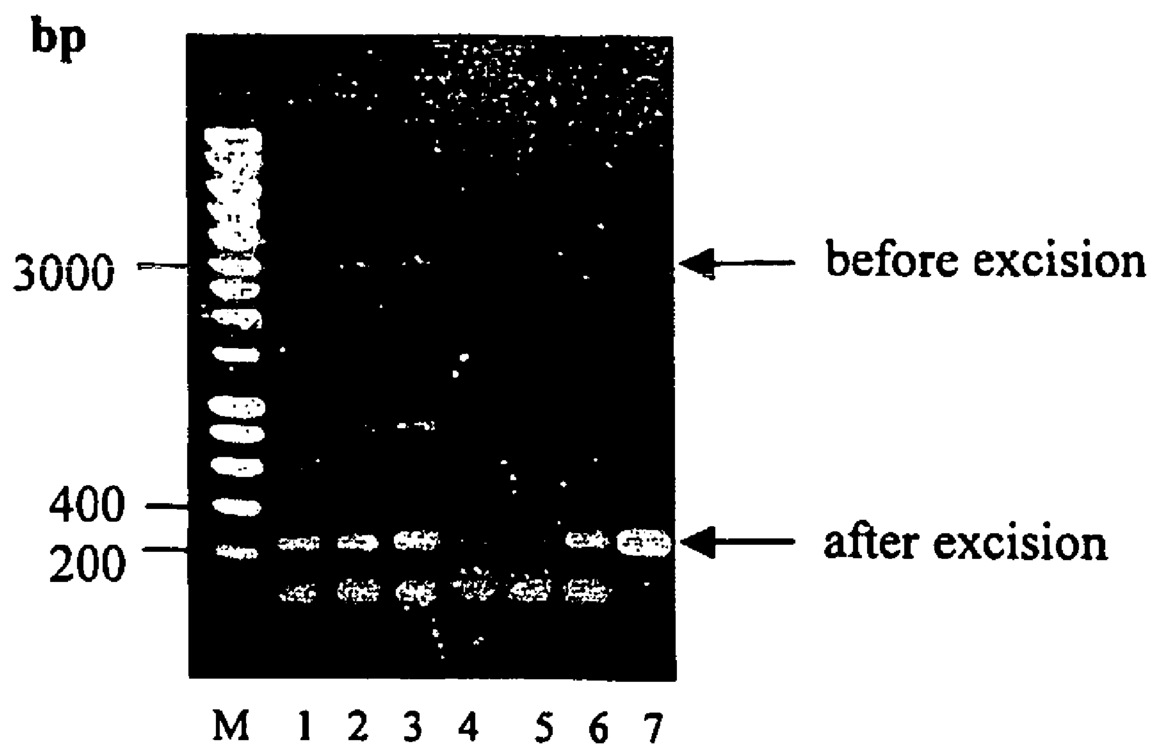
FIG. 9 shows PCR detection of germline excision of ZsGreen simple transposons, wherein: M=DNA marker (SmartLadder, Eurogentec); 1-7=DNA extracted from different pools of 7 F2 1125-12 flies (with DsRed); and Dro-12m-4 and su-a5c-r1 primers were used in these PCR reactions.
Figure 10:
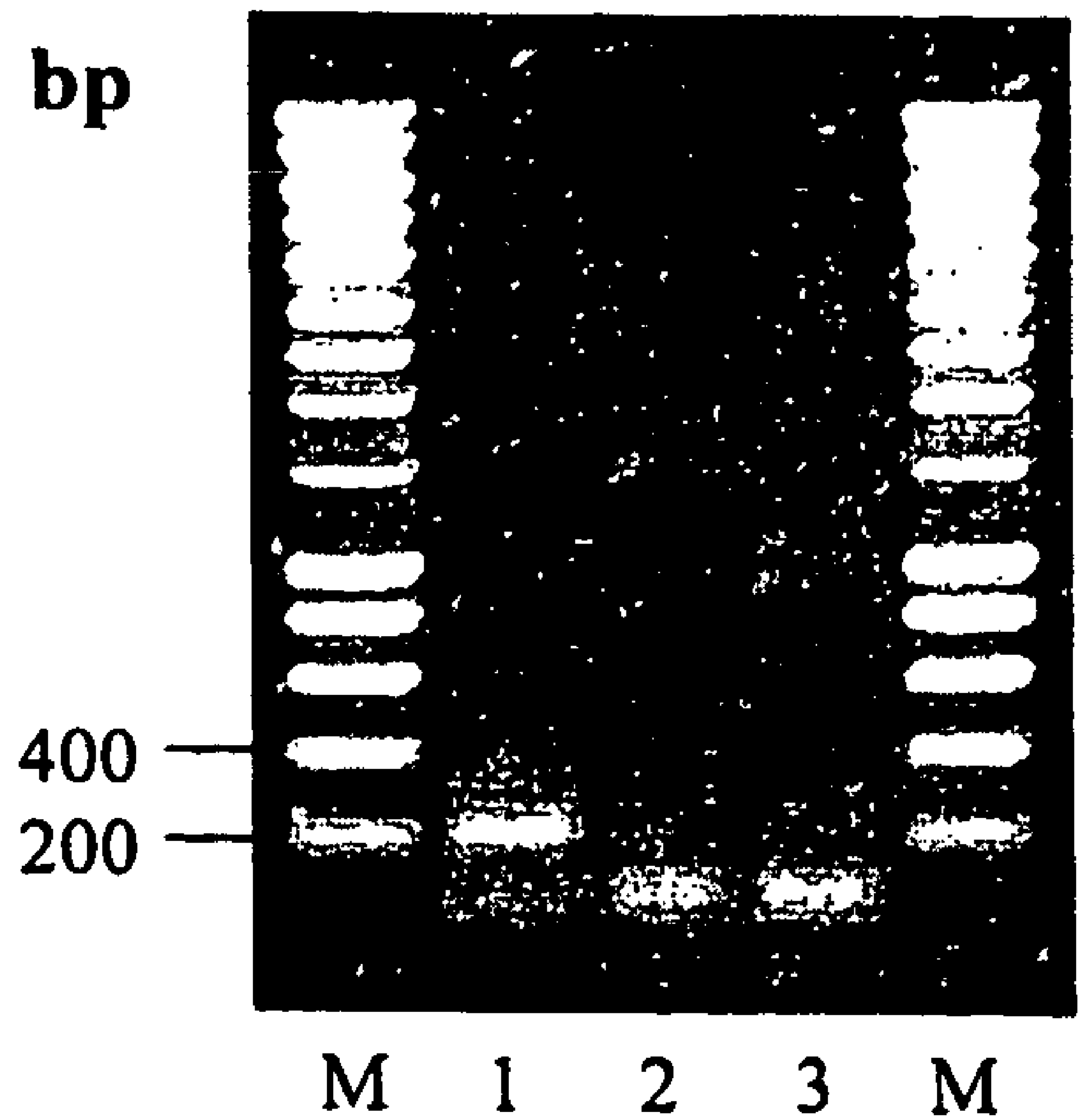
FIG. 10 shows the results of PCR analysis showing loss of piggyBac transposon sequence in DsRed stable transformant flies, wherein: M=DNA marker (SmartLadder, Eurogentec); 1=DNA from LA1125-12 flies unexposed to transposase used as positive control; 2=DNA from fly 70 (has neither ZsGreen nor AmCyan); and 3=DNA from fly 200 (has neither ZsGreen nar AmCyan).

```
<160> NUMBER OF SEQ ID NOS: 20

<210> SEQ ID NO 1
<211> LENGTH: 12
<212> TYPE: DNA
<213> ORGANISM: Artificial sequence
<220> FEATURE:
<223> OTHER INFORMATION: Synthetic

<400> SEQUENCE: 1

ttaattaatt aa                                                          12


<210> SEQ ID NO 2
<211> LENGTH: 12
<212> TYPE: DNA
<213> ORGANISM: Artificial sequence
<220> FEATURE:
<223> OTHER INFORMATION: Synthetic

<400> SEQUENCE: 2

ttaactagtt aa                                                          12


<210> SEQ ID NO 3
<211> LENGTH: 16157
<212> TYPE: DNA
<213> ORGANISM: Artificial sequence
<220> FEATURE:
<223> OTHER INFORMATION: Synthetic Construct Predicted sequence of
      pLA1025 construct

<400> SEQUENCE: 3

gggcaattcg ggcgcgcctc ttaattaagg cccccccctcg agaccatggt cgatcgacaa     60

acacgaaaat acattcctgg acagacctag ggtttgctc ttttttcttt gcaggatctg     120

gattcaacaa agaaggaaaa atctacggag tttggaacct catttattgc acgaagaaac     180

ttagagagaa agactgatgc ctaataaaga ctcaagctga ttgcaaaaac aatataaagt     240
```

```
tgtaccttat tgcggtgtca tcgtaaaacc aagatgctta aaagggatta ggcccactta    300

aattactgcg aaaaatttta tttacaaatt tctcacatga cttccagata aactaattaa    360

ctttgtgtgt caaggttgct tttccggcag aaaagtcaat ttgcaagtga tttaggtttt    420

tttaatgact atctttgcaa ttgaattggg tactattaga tattgaatat accaatattg    480

aggtataata caaatacaac aacatttgac ctcggcaact atcagaagta catgtaggtc    540

gggaacatta gggaattctg cgcgataagt tactaattat gctaagctat cgcagaacct    600

cattaagact tgagctgcag tgttttgcag gtacttatca tatttacagt attaatgtat    660

gcagtattat attaattcta aataagaaag tcaggagaag gatattcaaa actgaagaat    720

taatgtacat tagttttgtt tattagattt tcaatattgc agcatagaat atgtgtaagt    780

agtggagagc taaacgcgct tttcagaacg ttcatgctaa ttgctcatgg atctcacagg    840

aacaggtggt ggcggccctc ggtgcgctcg tactgctcca cgatggtgta gtcctcgttg    900

tgggaggtga tgtccagctt ggcgtccacg tagtagtagc cggcagctg cacgggcttc    960

ttggccatgt agatggactt gaactccacc aggtagtggc cgccgtcctt cagcttcagg   1020

gccttgtggg tctcgccctt cagcacgccg tcgcgggggt acaggcgctc ggtggaggcc   1080

tcccagccca tggtcttctt ctgcatcacg gggccgtcgg aggggaagtt cacgccgatg   1140

aacttcacct tgtagatgaa gcagccgtcc tgcagggagg agtcctgggt cacggtcgcc   1200

acgccgccgt cctcgaagtt catcacgcgc tcccacttga agccctcggg gaaggacagc   1260

ttcttgtagt cggggatgtc ggcggggtgc ttcacgtaca ccttggagcc gtactggaac   1320

tggggggaca ggatgtccca ggcgaagggc agggggccgc ccttggtcac cttcagcttc   1380

acggtgttgt ggccctcgta ggggcggccc tcgccctcgc cctcgatctc gaactcgtgg   1440

ccgttcacgg tgccctccat gcgcaccttg aagcgcatga actcggtgat gacgttctcg   1500

gaggaggcca ttctagccat tttggttcta gatccggggt ctctggatta gacgactgct   1560

ggctgatgga gcggctttgt gtcgggagga gtatccacac agcacaagaa ctcaaacggt   1620

agtgatatga aaactggtcc cgcagcccgt tttataaagc ccgcttagcg ctaaaacctt   1680

atcagccgca atgctctccg ctctcaagtc gcgttcaaaa cttttaccat atatgggtat   1740

gaattgttcg ccgattgggt tttcatttac ggagaatttc ctccgcaact gggtgttcgt   1800

gcttgtgtgt gtcttgtata tcgccatgaa gagtgtactt ccatgggtcc tatcagttgc   1860

ggcatgtgat tcaatttggg ggttactcat attcgatact tcagctggtt atctttatgc   1920

tgtgatggtc acggtgcttt tacacatttt ttccccaact actcattgta tgccaaaaca   1980

tacatatgta catgtgttta tagtgggttt attagtaatg tccagcgata ttaaaacatt   2040

acagttaaat aatattcata ttagcttacg tttactgcta tctgcacttc aaattggtta   2100

ttcaggggaca tttgtgcaac acacatcttc tagtaggggc atcactagtc gtagaaaaca   2160

cacctaactt aagccggttt taacaataac ggcgaaacag ctgccagacg agagaaaagt   2220

acacagcaag aagcatttct ataatgatgc cgtcctaaat atgcagcatt tttgctcaaa   2280

ttgatcattt cgttgcatcg ctcaggtggt atagtatttg gctattgaat gtgattgcta   2340

tcttaatagt tttgaatagt aatagtgcaa atattcattc ataaaaaata ggtaatcgat   2400

tttctcagtg cagtctatgc gtttgcgcaa acaggagacg aagagagaga cgcctcacac   2460

acaagcacat gcgtactacg ctggcctact ccgctactct atgtgtcgtc ctctgcatcg   2520

tctgcttggc ggcagttctt ccagaggctg tgacgtcagg taagctattt cgtctcggtg   2580

tgctgttagc ccgtaacgat aagctgtccg attcctaatt ctctttcaaa taatttgttt   2640
```

-continued

```
tatttttttt tttgtgtgtt ttgaagtcaa acagcttcat aaacaatatt aaatatcgca   2700
attgttattg caaatgcatt cgtatcaggc gccttgatgt ttttcggcca aaacttcgtc   2760
tgctctttgt cagcgtaatt gcgtttgccg gtcgtgccgt cttgctcgca cgcgcttgca   2820
aacaaaaagt gaaagaggga aagccactgt gttgttgctt ttgttgctat cgttggctgc   2880
acacacatgg caataagtaa ccatattgta gacttattta ttttagcgtt ttcgttgact   2940
aatctttgtt taaataattg cctatttcga gccaaaatga cgcataaagg acacggcaac   3000
atgcggtgcg ttgagcatgc gtacgagatg gcgctagaga gagcgagata aaaagaaaaa   3060
aacaaccggc gagtggcgag acacgaataa tacacacacg cacacatggt caaaggagtg   3120
gctccaacgt cggtgacgtc gcgcccagcc acagaccccg ccacgccccg ccccaccctt   3180
ccttccgctg ccccgcaccc ctttccttcc actaccgttt tgccgcattt ggtattgcca   3240
tctcgctttt ttggctttac tttgcttttt gaataagcca agaaactgaa atcaaagcgg   3300
acagtccgaa aattgaaact attccaaaaa acaacaaccg cacatgcact gcgttcggca   3360
aaagacgcag aaatcagcct gtggtctggc atcatcttaa aatatcatca gtatcatcat   3420
tgccattata aatacataag aaaatgagaa tacattaaag gtatatacat acaatctttg   3480
tcatagtcaa catattttgc aacaaaatta tctatagata acatgttttt gtagaaaatt   3540
ccactaactg attttcgtat aaatacaaat tattctcatt cttcaaaata ctcgccgacg   3600
tcatcgcgaa attcctcagc attcttcgac aaatgaagag agacagcgag tgacacaatc   3660
ttatcttacc gacgagtctt tgaaaatggc cccgggaacg gtgaaaaaca tatagccaag   3720
aatggagcga tcgccaggcg atggaaattg gcttcaaatt gctccgaata tggccagttg   3780
gtcagttggc attggattgt ggagagatac tagatcagct cgttctcctt ctcctccgca   3840
ttctcctact cgcccgaaga cgcttctttg atcgcttctt tctcgaatgt acatattgat   3900
atgtatttgg tgtttggcga cgatcagcca gctttaatgg ccataaaacg tgtcttggtt   3960
tgtgggccac ataacaggca gcgagatctg gaaaaatgat gtgacagtgg aaatgagaag   4020
taggtgcatc tgcaaagatt tgattcagag ttgatgccat tcatgatttt ttttagaagt   4080
atcatttgtg tttttagaat atagaattct agtatgtatg taagttaata aaacccattt   4140
ttgcggaaag tagataaaaa aaacattttt tttttttact gcactggata tctgcggccg   4200
gccagtttaa ccctagaaag ataatcatat tgtgacgtac gttaaagata atcatgcgta   4260
aaattgacgc atgggtacca gatatccagt gcagtaaaaa aaaaaaatgt tttttttatc   4320
tactttccgc aaaaatgggt tttattaact tacatacata ctagaattct aaaaaaaatc   4380
atgaatggca tcaactctga atcaaatctt tgcagatgca cctacttctc atttccactg   4440
tcacatcatt tttccagatc tcgctgcctg ttatgtggcc cacaaaccaa gacacgtttt   4500
atggccatta aagctggctg atcgtcgcca aacaccaaat acatatcaat atgtacattc   4560
gagaaagaag cgatcaaaga agcgtcttcg ggcgagtagg agaatgcgga ggagaaggag   4620
aacgagctga tctagtatct ctccacaatc caatgccaac tgaccaactg gccatattcg   4680
gagcaatttg aagccaattt ccatcgcctg gcgatcgctc cattcttggc tatatgtttt   4740
tcaccgttcc cggggccatt ttcaaagact cgtcggtaag ataagattgt gtcactcgct   4800
gtctctcttc atttgtcgaa gaatgctgag gaatttcgcg atgacgtcgg cgagtatttt   4860
gaagaatgag aataatttgt atttatacga aaatcagtta gtggaatttt ctacaaaaac   4920
atgttatcta tagataattt tgttgcaaaa tatgttgact atgacaaaga ttgtatgtat   4980
ataccttttaa tgtattctca ttttcttatg tatttataat ggcaatgatg atactgatga   5040
```

-continued

```
tattttaaga tgatgccaga ccacaggctg atttctgcgt cttttgccga acgcagtgca   5100
tgtgcggttg ttgtttttg gaatagtttc aattttcgga ctgtccgctt tgatttcagt   5160
ttcttggctt attcaaaaag caaagtaaag ccaaaaaagc gagatggcaa taccaaatgc   5220
ggcaaaacgg tagtggaagg aaaggggtgc ggggcagcgg aaggaagggt ggggcggggc   5280
gtggcggggt ctgtggctgg gcgcgacgtc accgacgttg gagccactcc tttgaccatg   5340
tgtgcgtgtg tgtattattc gtgtctcgcc actcgccggt tgttttttc tttttatctc   5400
gctctctcta gcgccatctc gtacgcatgc tcaacgcacc gcatgttgcc gtgtccttta   5460
tgcgtcattt tggctcgaaa taggcaatta tttaaacaaa gattagtcaa cgaaaacgct   5520
aaaataaata agtctacaat atggttactt attgccatgt gtgtgcagcc aacgatagca   5580
acaaaagcaa caacacagtg gctttccctc tttcactttt tgtttgcaag cgcgtgcgag   5640
caagacggca cgaccggcaa acgcaattac gctgacaaag agcagacgaa gttttggccg   5700
aaaaacatca aggcgcctga tacgaatgca tttgcaataa caattgcgat atttaatatt   5760
gtttatgaag ctgtttgact tcaaaacaca caaaaaaaaa aataaaacaa attatttgaa   5820
agagaattag gaatcggaca gcttatcgtt acgggctaac agcacaccga gacgaaatag   5880
cttacctgac gtcacagcct ctggaagaac tgccgccaag cagacgatgc agaggacgac   5940
acatagagta gcggagtagg ccagcgtagt acgcatgtgc ttgtgtgtga ggcgtctctc   6000
tcttcgtctc ctgtttgcgc aaacgcatag actgcactga gaaaatcgat tacctatttt   6060
ttatgaatga atatttgcac tattactatt caaaactatt aagatagcaa tcacattcaa   6120
tagccaaata ctataccacc tgagcgatgc aacgaaatga tcaatttgag caaaaatgct   6180
gcatatttag gacggcatca ttatagaaat gcttcttgct gtgtactttt ctctcgtctg   6240
gcagctgttt cgccgttatt gttaaaaccg gcttaagtta ggtgtgtttt ctacgactag   6300
tgatgcccct actagaagat gtgtgttgca caaatgtccc tgaataacca atttgaagtg   6360
cagatagcag taaacgtaag ctaatatgaa tattatttaa ctgtaatgtt ttaatatcgc   6420
tggacattac taataaaccc actataaaca catgtacata tgtatgtttt ggcatacaat   6480
gagtagttgg ggaaaaaatg tgtaaaagca ccgtgaccat cacagcataa agataaccag   6540
ctgaagtatc gaatatgagt aacccccaaa ttgaatcaca tgccgcaact gataggaccc   6600
atggaagtac actcttcatg gcgatataca agacacacac aagcacgaac acccagttgc   6660
ggaggaaatt ctccgtaaat gaaaacccaa tcggcgaaca attcataccc atatatggta   6720
aaagttttga acgcgacttg agagcggaga gcattgcggc tgataaggtt ttagcgctaa   6780
gcgggcttta taaaacgggc tgcgggacca gttttcatat cactaccgtt tgagttcttg   6840
tgctgtgtgg atactcctcc cgacacaaag ccgctccatc agccagcagt cgtctaatcc   6900
agagaccccg gatctagaac caaaatggct agcaaaggag aagaactttt cactggagtt   6960
gtcccaattc ttgttgaatt agatggtgat gttaatgggc acaaattttc tgtcagtgga   7020
gagggtgaag gtgatgcaac atacggaaaa cttaccctta aatttatttg cactactgga   7080
aaactacctg ttccatggcc aacacttgtc actactttca cttatggtgt tcaatgcttt   7140
tcaagatacc cagatcatat gaaacagcat gactttttca agagtgccat gcccgaaggt   7200
tatgtacagg aaagaactat atttttcaaa gatgacggga actacaagac acgtgctgaa   7260
gtcaagtttg aaggtgatac ccttgttaat agaatcgagt taaaaggtat tgattttaaa   7320
gaagatggaa acattcttgg acacaaattg gaatacaact ataactcaca caatgtatac   7380
atcatggcag acaaacaaaa gaatggaatc aaagttaact tcaaaattag acacaacatt   7440
```

```
gaagatggaa gcgttcaact agcagaccat tatcaacaaa atactccaat tggcgatggc   7500
cctgtccttt taccagacaa ccattacctg tccacacaat ctgccctttc gaaagatccc   7560
aacgaaaaga gagaccacat ggtccttctt gagtttgtaa cagctgctgg gattacacat   7620
ggcatggatg aactatacaa ataaggatcc atgagcaatt agcatgaacg ttctgaaaag   7680
cgcgtttagc tctccactac ttacacatat tctatgctgc aatattgaaa atctaataaa   7740
caaaactaat gtacattaat tcttcagttt tgaatatcct tctcctgact ttcttattta   7800
gaattaatat aatactgcat acattaatac tgtaaatatg ataagtacct gcaaaacact   7860
gcagctcaag tcttaatgag gttctgcgat agcttagcat aattagtaac ttatcgcgca   7920
gaattcccta atgttcccga cctacatgta cttctgatag ttgccgaggt caaatgttgt   7980
tgtatttgta ttatacctca atattggtat attcaatatc taatagtacc caattcaatt   8040
gcaaagatag tcattaaaaa aacctaaatc acttgcaaat tgacttttct gccggaaaag   8100
caaccttgac acacaaagtt aattagttta tctggaagtc atgtgagaaa tttgtaaata   8160
aaatttttcg cagtaattta agtgggccta atccctttta agcatcttgg ttttacgatg   8220
acaccgcaat aaggtacaac tttatattgt ttttgcaatc agcttgagtc tttattaggc   8280
atcagtcttt ctctctaagt ttcttcgtgc aataaatgag gttccaaact ccgtagattt   8340
ttccttcttt gttgaatcca gatcctgcaa agaaaaaaga gcaaacccct aggtctgtcc   8400
aggaatgtat tttcgtgttt gtcgatcgac catggtcacc ggtagatatc tataacaaga   8460
aaatatatat ataataagtt atcacgtaag tagaacatga aataacaata taattatcgt   8520
atgagttaaa tcttaaaagt cacgtaaaag ataatcatgc gtcattttga ctcacgcggt   8580
cgttatagtt caaaatcagt gacacttacc gcattgacaa gcacgcctca cgggagctcc   8640
aagcggcgac tgagatgtcc taaatgcaca gcgacggatt cgcgctattt agaaagagag   8700
agcaatattt caagaatgca tgcgtcaatt ttacgcagac tatctttcta gggttaagtc   8760
gacatccaca ttgtggccaa gctgtgtgac gcgacgcgcg ctaaagaatg gcaaaccaag   8820
tcgcgcgagc gtcgaaattc gtaatcatgg tcatagctgt ttcctgtgtg aaattgttat   8880
ccgctcacaa ttccacacaa catacgagcc ggaagcataa agtgtaaagc ctggggtgcc   8940
taatgagtga gctaactcac attaattgcg ttgcgctcac tgcccgcttt ccagtcggga   9000
aacctgtcgt gccagctgca ttaatgaatc ggccaacgcg cggggagagg cggtttgcgt   9060
attgggcgct cttccgcttc ctcgctcact gactcgctgc gctcggtcgt tcggctgcgg   9120
cgagcggtat cagctcactc aaaggcggta atacggttat ccacagaatc aggggataac   9180
gcaggaaaga acatgtgagc aaaaggccag caaaaggcca ggaaccgtaa aaaggccgcg   9240
ttgctggcgt ttttccatag gctccgcccc cctgacgagc atcacaaaaa tcgacgctca   9300
agtcagaggt ggcgaaaccc gacaggacta taaagatacc aggcgtttcc ccctggaagc   9360
tccctcgtgc gctctcctgt tccgaccctg ccgcttaccg gatacctgtc cgcctttctc   9420
ccttcgggaa gcgtggcgct ttctcaatgc tcacgctgta ggtatctcag ttcggtgtag   9480
gtcgttcgct ccaagctggg ctgtgtgcac gaaccccccg ttcagcccga ccgctgcgcc   9540
ttatccggta actatcgtct tgagtccaac ccggtaagac acgacttatc gccactggca   9600
gcagccactg gtaacaggat tagcagagcg aggtatgtag gcggtgctac agagttcttg   9660
aagtggtggc ctaactacgg ctacactaga aggacagtat ttggtatctg cgctctgctg   9720
aagccagtta ccttcggaaa aagagttggt agctcttgat ccggcaaaca aaccaccgct   9780
ggtagcggtg gtttttttgt ttgcaagcag cagattacgc gcagaaaaaa aggatctcaa   9840
```

```
gaagatcctt tgatcttttc tacggggtct gacgctcagt ggaacgaaaa ctcacgttaa   9900
gggattttgg tcatgagatt atcaaaaagg atcttcacct agatcctttt aaattaaaaa   9960
tgaagtttta aatcaatcta aagtatatat gagtaaactt ggtctgacag ttaccaatgc  10020
ttaatcagtg aggcacctat ctcagcgatc tgtctatttc gttcatccat agttgcctga  10080
ctccccgtcg tgtagataac tacgatacgg gagggcttac catctggccc cagtgctgca  10140
atgataccgc gagacccacg ctcaccggct ccagatttat cagcaataaa ccagccagcc  10200
ggaagggccg agcgcagaag tggtcctgca actttatccg cctccatcca gtctattaat  10260
tgttgccggg aagctagagt aagtagttcg ccagttaata gtttgcgcaa cgttgttgcc  10320
attgctacag gcatcgtggt gtcacgctcg tcgtttggta tggcttcatt cagctccggt  10380
tcccaacgat caaggcgagt tacatgatcc cccatgttgt gcaaaaaagc ggttagctcc  10440
ttcggtcctc cgatcgttgt cagaagtaag ttggccgcag tgttatcact catggttatg  10500
gcagcactgc ataattctct tactgtcatg ccatccgtaa gatgcttttc tgtgactggt  10560
gagtactcaa ccaagtcatt ctgagaatag tgtatgcggc gaccgagttg ctcttgcccg  10620
gcgtcaatac gggataatac cgcgccacat agcagaactt taaaagtgct catcattgga  10680
aaacgttctt cggggcgaaa actctcaagg atcttaccgc tgttgagatc cagttcgatg  10740
taacccactc gtgcacccaa ctgatcttca gcatctttta ctttcaccag cgtttctggg  10800
tgagcaaaaa caggaaggca aaatgccgca aaaaagggaa taagggcgac acggaaatgt  10860
tgaatactca tactcttcct ttttcaatat tattgaagca tttatcaggg ttattgtctc  10920
atgagcggat acatatttga atgtatttag aaaaataaac aaataggggt tccgcgcaca  10980
tttccccgaa aagtgccacc tgacgtctaa gaaaccatta ttatcatgac attaacctat  11040
aaaaataggc gtatcacgag gccctttcgt ctcgcgcgtt tcggtgatga cggtgaaaac  11100
ctctgacaca tgcagctccc ggagacggtc acagcttgtc tgtaagcgga tgccgggagc  11160
agacaagccc gtcagggcgc gtcagcgggt gttggcgggt gtcggggctg gcttaactat  11220
gcggcatcag agcagattgt actgagagtg caccatatat gcggtgtgaa ataccgcaca  11280
gatgcgtaag gagaaaatac cgcatcaggc gccattcgcc attcaggctg cgcaactgtt  11340
gggaagggcg atcggtgcgg gcctcttcgc tattacgcca gctggcgaaa gggggatgtg  11400
ctgcaaggcg attaagttgg gtaacgccag ggttttccca gtcacgacgt tgtaaaacga  11460
cggccagtgc caagctttgt ttaaaatata acaaaattgt gatcccacaa aatgaagtgg  11520
ggcaaaatca aataattaat agtgtccgta aacttgttgg tcttcaactt tttgaggaac  11580
acgttggacg gcaaatccgt gactataaca caagttgatt taataatttt agccaacacg  11640
tcgggctgcg tgtttttttgc cgacgcgtct gtgtacacgt tgattaactg gtcgattaaa  11700
ctgttgaaat aatttaattt ttggttcttc tttaaatctg tgatgaaatt ttttaaaata  11760
actttaaatt cttcattggt aaaaaatgcc acgttttgca acttgtgagg gtctaatatg  11820
aggtcaaact cagtaggagt tttatccaaa aaagaaaaca tgattacgtc tgtacacgaa  11880
cgcgtattaa cgcagagtgc aaagtataag agggttaaaa aatatatttt acgcaccata  11940
tacgcatcgg gttgatatcg ttaatatgga tcaatttgaa cagttgatta acgtgtctct  12000
gctcaagtct ttgatcaaaa cgcaaatcga cgaaaatgtg tcggacaata tcaagtcgat  12060
gagcgaaaaa ctaaaaaggc tagaatacga caatctcaca gacagcgttg agatatacgg  12120
tattcacgac agcaggctga ataataaaaa aattagaaac tattatttaa ccctagaaag  12180
ataatcatat tgtgacgtac gttaaagata atcatgcgta aaattgacgc atgtgtttta  12240
```

```
tcggtctgta tatcgaggtt tatttattaa tttgaataga tattaagttt tattatattt  12300
acacttacat actaataata aattcaacaa acaatttatt tatgtttatt tatttattaa  12360
aaaaaaacaa aaactcaaaa tttcttctat aaagtaacaa aacttttaaa cattctctct  12420
tttacaaaaa taaacttatt ttgtacttta aaaacagtca tgttgtatta taaaataagt  12480
aattagctta acttatacat aatagaaaca aattatactt attagtcagt cagaaacaac  12540
tttggcacat atcaatatta tgctctcgac aaataacttt tttgcatttt ttgcacgatg  12600
catttgcctt tcgccttatt ttagaggggc agtaagtaca gtaagtacgt tttttcatta  12660
ctggctcttc agtactgtca tctgatgtac caggcacttc atttggcaaa atattagaga  12720
tattatcgcg caaatatctc ttcaaagtag gagcttctaa acgcttacgc ataaacgatg  12780
acgtcaggct catgtaaagg tttctcataa attttttgcg actttggacc ttttctccct  12840
tgctactgac attatggctg tatataataa aagaatttat gcaggcaatg tttatcattc  12900
cgtacaataa tgccataggc cacctattcg tcttcctact gcaggtcatc acagaacaca  12960
tttggtctag cgtgtccact ccgcctttag tttgattata atacataacc atttgcggtt  13020
taccgggcgc ctcttaatta aggccccccc tcgagaccat ggtcgatcga caaacacgaa  13080
aatacattcc tggacagacc taggggtttg ctctttttc tttgcaggat ctggattcaa  13140
caaagaagga aaaatctacg gagtttggaa cctcatttat tgcacgaaga aacttagaga  13200
gaaagactga tgcctaataa agactcaagc tgattgcaaa aacaatataa agttgtacct  13260
tattgcggtg tcatcgtaaa accaagatgc ttaaaaggga ttaggcccac ttaaattact  13320
gcgaaaaatt ttatttacaa atttctcaca tgacttccag ataaactaat taactttgtg  13380
tgtcaaggtt gcttttccgg cagaaaagtc aatttgcaag tgatttaggt ttttttaatg  13440
actatctttg caattgaatt gggtactatt agatattgaa tataccaata ttgaggtata  13500
atacaaatac aacaacattt gacctcggca actatcagaa gtacatgtag gtcgggaaca  13560
ttagggaatt ctgcgcgata agttactaat tatgctaagc tatcgcagaa cctcattaag  13620
acttgagctg cagtgttttg caggtactta tcatatttac agtattaatg tatgcagtat  13680
tatattaatt ctaaataaga aagtcaggag aaggatattc aaaactgaag aattaatgta  13740
cattagtttt gtttattaga ttttcaatat tgcagcatag aatatgtgta agtagtggag  13800
agctaaacgc gcttttcaga acgttcatgc taattgctca tggatctcac aggaacaggt  13860
ggtggcggcc ctcggtgcgc tcgtactgct ccacgatggt gtagtcctcg ttgtgggagg  13920
tgatgtccag cttggcgtcc acgtagtagt agccgggcag ctgcacgggc ttcttggcca  13980
tgtagatgga cttgaactcc accaggtagt ggccgccgtc cttcagcttc agggccttgt  14040
gggtctcgcc cttcagcacg ccgtcgcggg ggtacaggcg ctcggtggag gcctcccagc  14100
ccatggtctt cttctgcatc acggggccgt cggaggggaa gttcacgccg atgaacttca  14160
ccttgtagat gaagcagccg tcctgcaggg aggagtcctg ggtcacggtc gccacgccgc  14220
cgtcctcgaa gttcatcacg cgctcccact tgaagccctc ggggaaggac agcttcttgt  14280
agtcggggat gtcggcgggg tgcttcacgt acaccttgga gccgtactgg aactgggggg  14340
acaggatgtc ccaggcgaag ggcagggggc cgcccttggt caccttcagc ttcacggtgt  14400
tgtggccctc gtaggggcgg ccctcgccct cgccctcgat ctcgaactcg tggccgttca  14460
cggtgccctc catgcgcacc ttgaagcgca tgaactcggt gatgacgttc tcggaggagg  14520
ccattctagc cattttggtt ctagatggca gttgtttatc tggaagggag atggaagtgc  14580
actcggttag ctcgatctgt cgattatata tgtaaagttt tatagctccc acctacatct  14640
```

```
caattcttta aattctacta ctttaatgac aacatagaaa actaatttgt gtctcaagaa  14700

aatatttaac tttttaagat attgaagaag tgaagtgaaa ctctattgtc catttgagca  14760

catttcagta aataaaacca tgaaaaattg ccaaaattgg tatattccat ttccttttga  14820

gtcatgctaa ttggttattc acttgaaact aaatcagtgc tctaaaaata tcggaaaaga  14880

atagttcata gaacttaatt taaacgtatc aaattaattg aaaatacgtt tcgttgcaat  14940

tactcttcac tttatattta gatattgaac tttcgaagac cgattagtga cttgtagaaa  15000

aatccatcaa acaatccgaa cttattaaaa agagttttaa tatccttagt cctcttggct  15060

ttttctgtaa taatccttgg atccttcgac attgaggtcg cactcacaca ccttttaggt  15120

caacgaaagg agaaaaattg gatagagtcg cacgttcgat tcctgttgac aactagattc  15180

aacaacaaat ggcacgccga tcggtctgtc ctgcctttat atctcggctc tccctcgaag  15240

cgatttgagt tggatgccag tgcggcactg agaaaaagat tgagcgaaag tgctgcggaa  15300

caatcaactc gaatcgatcc atataagcag ttttcagact tctggccgag catgtcagaa  15360

gtttggatgc ctcattgcac gaagacgact cattaatgcg cttcacaaaa aaaggaagcc  15420

acacaattaa atacttaata aagcatagaa tcatttatta agattaccaa taaattcaat  15480

aaacgaggga atttccaaac tgcgaaaata tgacatttta tattttttttc acattgttag  15540

taggtacaaa tcctagaaaa tggtctcata acatataaca gcttaaataa ctatgtagta  15600

gaagataaac tttatgttca attcagttca tatttaatcc tagaaatatt taattaattg  15660

acaatatatg atggaagtaa gctatcaatc ttaggaccct attcattatt tgtagggagt  15720

gccaggagag agaaagctct cgaaagataa gagaacgcca tagccgagtg attagcagag  15780

gtgcgtgata gtcggtgtat gggccaccta aacggcaatc agcactctcg agtggccaat  15840

tagccccatc tccgtcccca tctctgtccc aatcctgctg ccaatgggcg actgctgcgg  15900

cggacgactc attcggtgct gagagttcgg aaaatagaaa cggaccttag aaggaccgac  15960

gcaagacaat tggcatccgc ggcagggact gggagaatgg gacatttcaa cgggcacgca  16020

gcgaggcgaa tctaaaatag acgcgccaag cagagcggca cctataaatc aacatcaagg  16080

ttgatcgaga tatccaccca tctgcggccg ccatgcgtca attttacgca gactatcttt  16140

ctagggttaa tcagccc                                                 16157
```

<210> SEQ ID NO 4
<211> LENGTH: 16157
<212> TYPE: DNA
<213> ORGANISM: Artificial sequence
<220> FEATURE:
<223> OTHER INFORMATION: Synthetic Construct Predicted sequence of pLA1125 construct

<400> SEQUENCE: 4

```
gggcaattcg ggcgcgcctc ttaattaagg cccccccctcg agaccatggt cgatcgacaa     60

acacgaaaat acattcctgg acagacctag gggtttgctc tttttctttt gcaggatctg    120

gattcaacaa agaaggaaaa atctacggag tttggaacct catttattgc acgaagaaac    180

ttagagagaa agactgatgc ctaataaaga ctcaagctga ttgcaaaaac aatataaagt    240

tgtaccttat tgcggtgtca tcgtaaaacc aagatgctta aaagggatta ggcccactta    300

aattactgcg aaaaatttta tttacaaatt tctcacatga cttccagata aactaattaa    360

ctttgtgtgt caaggttgct ttccggcag aaaagtcaat ttgcaagtga tttaggtttt    420

tttaatgact atctttgcaa ttgaattggg tactattaga tattgaatat accaatattg    480
```

-continued

```
aggtataata caaatacaac aacatttgac ctcggcaact atcagaagta catgtaggtc    540
gggaacatta gggaattctg cgcgataagt tactaattat gctaagctat cgcagaacct    600
cattaagact tgagctgcag tgttttgcag gtacttatca tatttacagt attaatgtat    660
gcagtattat attaattcta aataagaaag tcaggagaag gatattcaaa actgaagaat    720
taatgtacat tagttttgtt tattagattt tcaatattgc agcatagaat atgtgtaagt    780
agtggagagc taaacgcgct tttcagaacg ttcatgctaa ttgctcatgg atctcacagg    840
aacaggtggt ggcggccctc ggtgcgctcg tactgctcca cgatggtgta gtcctcgttg    900
tgggaggtga tgtccagctt ggcgtccacg tagtagtagc cgggcagctg cacgggcttc    960
ttggccatgt agatggactt gaactccacc aggtagtggc cgccgtcctt cagcttcagg   1020
gccttgtggg tctcgccctt cagcacgccg tcgcgggggt acaggcgctc ggtggaggcc   1080
tcccagccca tggtcttctt ctgcatcacg gggccgtcgg aggggaagtt cacgccgatg   1140
aacttcacct tgtagatgaa gcagccgtcc tgcagggagg agtcctgggt cacggtcgcc   1200
acgccgccgt cctcgaagtt catcacgcgc tcccacttga agccctcggg gaaggacagc   1260
ttcttgtagt cggggatgtc ggcggggtgc ttcacgtaca ccttggagcc gtactggaac   1320
tggggggaca ggatgtccca ggcgaagggc agggggccgc ccttggtcac cttcagcttc   1380
acggtgttgt ggccctcgta ggggcggccc tcgccctcgc cctcgatctc gaactcgtgg   1440
ccgttcacgg tgccctccat gcgcaccttg aagcgcatga actcggtgat gacgttctcg   1500
gaggaggcca ttctagccat tttggttcta gatccggggt ctctggatta gacgactgct   1560
ggctgatgga gcggctttgt gtcgggagga gtatccacac agcacaagaa ctcaaacggt   1620
agtgatatga aaactggtcc cgcagcccgt tttataaagc ccgcttagcg ctaaaacctt   1680
atcagccgca atgctctccg ctctcaagtc gcgttcaaaa cttttaccat atatgggtat   1740
gaattgttcg ccgattgggt tttcatttac ggagaatttc ctccgcaact gggtgttcgt   1800
gcttgtgtgt gtcttgtata tcgccatgaa gagtgtactt ccatgggtcc tatcagttgc   1860
ggcatgtgat tcaatttggg ggttactcat attcgatact tcagctggtt atctttatgc   1920
tgtgatggtc acggtgcttt tacacatttt ttccccaact actcattgta tgccaaaaca   1980
tacatatgta catgtgttta tagtgggttt attagtaatg tccagcgata ttaaaacatt   2040
acagttaaat aatattcata ttagcttacg tttactgcta tctgcacttc aaattggtta   2100
ttcagggaca tttgtgcaac acacatcttc tagtaggggc atcactagtc gtagaaaaca   2160
cacctaactt aagccggttt taacaataac ggcgaaacag ctgccagacg agagaaaagt   2220
acacagcaag aagcatttct ataatgatgc cgtcctaaat atgcagcatt tttgctcaaa   2280
ttgatcattt cgttgcatcg ctcaggtggt atagtatttg gctattgaat gtgattgcta   2340
tcttaatagt tttgaatagt aatagtgcaa atattcattc ataaaaaata ggtaatcgat   2400
tttctcagtg cagtctatgc gtttgcgcaa acaggagacg aagagagaga cgcctcacac   2460
acaagcacat gcgtactacg ctggcctact ccgctactct atgtgtcgtc ctctgcatcg   2520
tctgcttggc ggcagttctt ccagaggctg tgacgtcagg taagctattt cgtctcggtg   2580
tgctgttagc ccgtaacgat aagctgtccg attcctaatt ctctttcaaa taatttgttt   2640
tatttttttt tttgtgtgtt ttgaagtcaa acagcttcat aaacaatatt aaatatcgca   2700
attgttattg caaatgcatt cgtatcaggc gccttgatgt ttttcggcca aaacttcgtc   2760
tgctctttgt cagcgtaatt gcgtttgccg gtcgtgccgt cttgctcgca cgcgcttgca   2820
aacaaaaagt gaaagaggga aagccactgt gttgttgctt ttgttgctat cgttggctgc   2880
```

```
acacacatgg caataagtaa ccatattgta gacttattta ttttagcgtt ttcgttgact   2940
aatctttgtt taaataattg cctatttcga gccaaaatga cgcataaagg acacggcaac   3000
atgcggtgcg ttgagcatgc gtacgagatg gcgctagaga gagcgagata aaaagaaaaa   3060
aacaaccggc gagtggcgag acacgaataa tacacacacg cacacatggt caaaggagtg   3120
gctccaacgt cggtgacgtc gcgcccagcc acagaccccg ccacgccccg ccccaccctt   3180
ccttccgctg ccccgcaccc ctttccttcc actaccgttt tgccgcattt ggtattgcca   3240
tctcgctttt ttggctttac tttgcttttt gaataagcca agaaactgaa atcaaagcgg   3300
acagtccgaa aattgaaact attccaaaaa acaacaaccg cacatgcact gcgttcggca   3360
aaagacgcag aaatcagcct gtggtctggc atcatcttaa aatatcatca gtatcatcat   3420
tgccattata aatacataag aaaatgagaa tacattaaag gtatatacat acaatctttg   3480
tcatagtcaa catattttgc aacaaaatta tctatagata acatgttttt gtagaaaatt   3540
ccactaactg attttcgtat aaatacaaat tattctcatt cttcaaaata ctcgccgacg   3600
tcatcgcgaa attcctcagc attcttcgac aaatgaagag agacagcgag tgacacaatc   3660
ttatcttacc gacgagtctt tgaaaatggc cccgggaacg gtgaaaaaca tatagccaag   3720
aatggagcga tcgccaggcg atggaaattg gcttcaaatt gctccgaata tggccagttg   3780
gtcagttggc attggattgt ggagagatac tagatcagct cgttctcctt ctcctccgca   3840
ttctcctact cgcccgaaga cgcttctttg atcgcttctt tctcgaatgt acatattgat   3900
atgtatttgg tgtttggcga cgatcagcca gctttaatgg ccataaaacg tgtcttggtt   3960
tgtgggccac ataacaggca gcgagatctg gaaaaatgat gtgacagtgg aaatgagaag   4020
taggtgcatc tgcaaagatt tgattcagag ttgatgccat tcatgatttt ttttagaagt   4080
atcatttgtg tttttagaat atagaattct agtatgtatg taagttaata aaacccattt   4140
ttgcggaaag tagataaaaa aaacattttt tttttttact gcactggata tctgcggccg   4200
gccagtttaa ccctagaaag ataatcatat tgtgacgtac gttaaagata atcatgcgta   4260
aaattgacgc atgggtacca gatatccagt gcagtaaaaa aaaaaaaatgt ttttttttatc   4320
tactttccgc aaaaatgggt tttattaact tacatacata ctagaattct aaaaaaaaatc   4380
atgaatggca tcaactctga atcaaatctt tgcagatgca cctacttctc atttccactg   4440
tcacatcatt tttccagatc tcgctgcctg ttatgtggcc cacaaaccaa gacacgtttt   4500
atggccatta aagctggctg atcgtcgcca aacaccaaat acatatcaat atgtacattc   4560
gagaaagaag cgatcaaaga agcgtcttcg ggcgagtagg agaatgcgga ggagaaggag   4620
aacgagctga tctagtatct ctccacaatc caatgccaac tgaccaactg gccatattcg   4680
gagcaatttg aagccaattt ccatcgcctg gcgatcgctc cattcttggc tatatgtttt   4740
tcaccgttcc cggggccatt ttcaaagact cgtcggtaag ataagattgt gtcactcgct   4800
gtctctcttc atttgtcgaa gaatgctgag gaatttcgcg atgacgtcgg cgagtatttt   4860
gaagaatgag aataatttgt atttatacga aaatcagtta gtggaatttt ctacaaaaac   4920
atgttatcta tagataattt tgttgcaaaa tatgttgact atgacaaaga ttgtatgtat   4980
ataccttttaa tgtattctca ttttcttatg tatttataat ggcaatgatg atactgatga   5040
tattttaaga tgatgccaga ccacaggctg atttctgcgt cttttgccga acgcagtgca   5100
tgtgcggttg ttgtttttttg gaatagtttc aattttcgga ctgtccgctt tgatttcagt   5160
ttcttggctt attcaaaaag caaagtaaag ccaaaaaagc gagatggcaa taccaaatgc   5220
ggcaaaacgg tagtggaagg aaaggggtgc ggggcagcgg aaggaagggt ggggcggggc   5280
```

```
gtggcggggt ctgtggctgg gcgcgacgtc accgacgttg gagccactcc tttgaccatg   5340

tgtgcgtgtg tgtattattc gtgtctcgcc actcgccggt tgtttttttc tttttatctc   5400

gctctctcta gcgccatctc gtacgcatgc tcaacgcacc gcatgttgcc gtgtccttta   5460

tgcgtcattt tggctcgaaa taggcaatta tttaaacaaa gattagtcaa cgaaaacgct   5520

aaaataaata agtctacaat atggttactt attgccatgt gtgtgcagcc aacgatagca   5580

acaaaagcaa caacacagtg gctttccctc tttcactttt tgtttgcaag cgcgtgcgag   5640

caagacggca cgaccggcaa acgcaattac gctgacaaag agcagacgaa gttttggccg   5700

aaaaacatca aggcgcctga tacgaatgca tttgcaataa caattgcgat atttaatatt   5760

gtttatgaag ctgtttgact tcaaaacaca caaaaaaaaa aataaaacaa attatttgaa   5820

agagaattag gaatcggaca gcttatcgtt acgggctaac agcacaccga gacgaaatag   5880

cttacctgac gtcacagcct ctggaagaac tgccgccaag cagacgatgc agaggacgac   5940

acatagagta gcggagtagg ccagcgtagt acgcatgtgc ttgtgtgtga ggcgtctctc   6000

tcttcgtctc ctgtttgcgc aaacgcatag actgcactga gaaaatcgat tacctatttt   6060

ttatgaatga atatttgcac tattactatt caaaactatt aagatagcaa tcacattcaa   6120

tagccaaata ctataccacc tgagcgatgc aacgaaatga tcaatttgag caaaaatgct   6180

gcatatttag gacggcatca ttatagaaat gcttcttgct gtgtactttt ctctcgtctg   6240

gcagctgttt cgccgttatt gttaaaaccg gcttaagtta ggtgtgtttt ctacgactag   6300

tgatgcccct actagaagat gtgtgttgca caaatgtccc tgaataacca atttgaagtg   6360

cagatagcag taaacgtaag ctaatatgaa tattatttaa ctgtaatgtt ttaatatcgc   6420

tggacattac taataaaccc actataaaca catgtacata tgtatgtttt ggcatacaat   6480

gagtagttgg ggaaaaaatg tgtaaaagca ccgtgaccat cacagcataa agataaccag   6540

ctgaagtatc gaatatgagt aacccccaaa ttgaatcaca tgccgcaact gataggaccc   6600

atggaagtac actcttcatg gcgatataca agacacacac aagcacgaac acccagttgc   6660

ggaggaaatt ctccgtaaat gaaaacccaa tcggcgaaca attcataccc atatatggta   6720

aaagttttga acgcgacttg agagcggaga gcattgcggc tgataaggtt ttagcgctaa   6780

gcgggcttta taaaacgggc tgcgggacca gttttcatat cactaccgtt tgagttcttg   6840

tgctgtgtgg atactcctcc cgacacaaag ccgctccatc agccagcagt cgtctaatcc   6900

agagaccccg gatctagaac caaaatggct agcaaaggag aagaactttt cactggagtt   6960

gtcccaattc ttgttgaatt agatggtgat gttaatgggc acaaattttc tgtcagtgga   7020

gagggtgaag gtgatgcaac atacggaaaa cttaccctta aatttatttg cactactgga   7080

aaactacctg ttccatggcc aacacttgtc actactttca cttatggtgt tcaatgcttt   7140

tcaagatacc cagatcatat gaaacagcat gactttttca agagtgccat gcccgaaggt   7200

tatgtacagg aaagaactat atttttcaaa gatgacggga actacaagac acgtgctgaa   7260

gtcaagtttg aaggtgatac ccttgttaat agaatcgagt taaaaggtat tgattttaaa   7320

gaagatggaa acattcttgg acacaaattg gaatacaact ataactcaca caatgtatac   7380

atcatggcag acaaacaaaa gaatggaatc aaagttaact tcaaaattag acacaacatt   7440

gaagatggaa gcgttcaact agcagaccat tatcaacaaa atactccaat tggcgatggc   7500

cctgtccttt taccagacaa ccattacctg tccacacaat ctgccctttc gaaagatccc   7560

aacgaaaaga gagaccacat ggtccttctt gagtttgtaa cagctgctgg gattacacat   7620

ggcatggatg aactatacaa ataaggatcc atgagcaatt agcatgaacg ttctgaaaag   7680
```

```
cgcgtttagc tctccactac ttacacatat tctatgctgc aatattgaaa atctaataaa   7740
caaaactaat gtacattaat tcttcagttt tgaatatcct tctcctgact ttcttattta   7800
gaattaatat aatactgcat acattaatac tgtaaatatg ataagtacct gcaaaacact   7860
gcagctcaag tcttaatgag gttctgcgat agcttagcat aattagtaac ttatcgcgca   7920
gaattcccta atgttcccga cctacatgta cttctgatag ttgccgaggt caaatgttgt   7980
tgtatttgta ttatacctca atattggtat attcaatatc taatagtacc caattcaatt   8040
gcaaagatag tcattaaaaa aacctaaatc acttgcaaat tgacttttct gccggaaaag   8100
caaccttgac acacaaagtt aattagttta tctggaagtc atgtgagaaa tttgtaaata   8160
aaatttttcg cagtaattta agtgggccta atcccttta agcatcttgg ttttacgatg   8220
acaccgcaat aaggtacaac tttatattgt ttttgcaatc agcttgagtc tttattaggc   8280
atcagtcttt ctctctaagt ttcttcgtgc aataaatgag gttccaaact ccgtagattt   8340
ttccttcttt gttgaatcca gatcctgcaa agaaaaaaga gcaaacccct aggtctgtcc   8400
aggaatgtat tttcgtgttt gtcgatcgac catggtcacc ggtagatatc tataacaaga   8460
aaatatatat ataataagtt atcacgtaag tagaacatga aataacaata taattatcgt   8520
atgagttaaa tcttaaaagt cacgtaaaag ataatcatgc gtcattttga ctcacgcggt   8580
cgttatagtt caaaatcagt gacacttacc gcattgacaa gcacgcctca cgggagctcc   8640
aagcggcgac tgagatgtcc taaatgcaca gcgacggatt cgcgctattt agaaagagag   8700
agcaatattt caagaatgca tgcgtcaatt ttacgcagac tatctttcta gggttaagtc   8760
gacatccaca ttgtggccaa gctgtgtgac gcgacgcgcg ctaaagaatg gcaaaccaag   8820
tcgcgcgagc gtcgaaattc gtaatcatgg tcatagctgt ttcctgtgtg aaattgttat   8880
ccgctcacaa ttccacacaa catacgagcc ggaagcataa agtgtaaagc ctggggtgcc   8940
taatgagtga gctaactcac attaattgcg ttgcgctcac tgcccgcttt ccagtcggga   9000
aacctgtcgt gccagctgca ttaatgaatc ggccaacgcg cggggagagg cggtttgcgt   9060
attgggcgct cttccgcttc ctcgctcact gactcgctgc gctcggtcgt tcggctgcgg   9120
cgagcggtat cagctcactc aaaggcggta atacggttat ccacagaatc aggggataac   9180
gcaggaaaga acatgtgagc aaaaggccag caaaaggcca ggaaccgtaa aaaggccgcg   9240
ttgctggcgt ttttccatag gctccgcccc cctgacgagc atcacaaaaa tcgacgctca   9300
agtcagaggt ggcgaaaccc gacaggacta taaagatacc aggcgtttcc ccctggaagc   9360
tccctcgtgc gctctcctgt tccgaccctg ccgcttaccg gatacctgtc cgcctttctc   9420
ccttcgggaa gcgtggcgct ttctcaatgc tcacgctgta ggtatctcag ttcggtgtag   9480
gtcgttcgct ccaagctggg ctgtgtgcac gaaccccccg ttcagcccga ccgctgcgcc   9540
ttatccggta actatcgtct tgagtccaac ccggtaagac acgacttatc gccactggca   9600
gcagccactg gtaacaggat tagcagagcg aggtatgtag gcggtgctac agagttcttg   9660
aagtggtggc ctaactacgg ctacactaga aggacagtat ttggtatctg cgctctgctg   9720
aagccagtta ccttcggaaa aagagttggt agctcttgat ccggcaaaca aaccaccgct   9780
ggtagcggtg gtttttttgt ttgcaagcag cagattacgc gcagaaaaaa aggatctcaa   9840
gaagatcctt tgatcttttc tacggggtct gacgctcagt ggaacgaaaa ctcacgttaa   9900
gggattttgg tcatgagatt atcaaaaagg atcttcacct agatcctttt aaattaaaaa   9960
tgaagtttta aatcaatcta aagtatatat gagtaaactt ggtctgacag ttaccaatgc  10020
ttaatcagtg aggcacctat ctcagcgatc tgtctatttc gttcatccat agttgcctga  10080
```

```
ctccccgtcg tgtagataac tacgatacgg gagggcttac catctggccc cagtgctgca  10140

atgataccgc gagacccacg ctcaccggct ccagatttat cagcaataaa ccagccagcc  10200

ggaagggccg agcgcagaag tggtcctgca actttatccg cctccatcca gtctattaat  10260

tgttgccggg aagctagagt aagtagttcg ccagttaata gtttgcgcaa cgttgttgcc  10320

attgctacag gcatcgtggt gtcacgctcg tcgtttggta tggcttcatt cagctccggt  10380

tcccaacgat caaggcgagt tacatgatcc cccatgttgt gcaaaaaagc ggttagctcc  10440

ttcggtcctc cgatcgttgt cagaagtaag ttggccgcag tgttatcact catggttatg  10500

gcagcactgc ataattctct tactgtcatg ccatccgtaa gatgcttttc tgtgactggt  10560

gagtactcaa ccaagtcatt ctgagaatag tgtatgcggc gaccgagttg ctcttgcccg  10620

gcgtcaatac gggataatac cgcgccacat agcagaactt taaaagtgct catcattgga  10680

aaacgttctt cggggcgaaa actctcaagg atcttaccgc tgttgagatc cagttcgatg  10740

taacccactc gtgcacccaa ctgatcttca gcatctttta ctttcaccag cgtttctggg  10800

tgagcaaaaa caggaaggca aaatgccgca aaaaagggaa taagggcgac acggaaatgt  10860

tgaatactca tactcttcct ttttcaatat tattgaagca tttatcaggg ttattgtctc  10920

atgagcggat acatatttga atgtatttag aaaaataaac aaataggggt tccgcgcaca  10980

tttccccgaa aagtgccacc tgacgtctaa gaaaccatta ttatcatgac attaacctat  11040

aaaaataggc gtatcacgag gccctttcgt ctcgcgcgtt tcggtgatga cggtgaaaac  11100

ctctgacaca tgcagctccc ggagacggtc acagcttgtc tgtaagcgga tgccgggagc  11160

agacaagccc gtcagggcgc gtcagcgggt gttggcgggt gtcggggctg gcttaactat  11220

gcggcatcag agcagattgt actgagagtg caccatatat gcggtgtgaa ataccgcaca  11280

gatgcgtaag gagaaaatac cgcatcaggc gccattcgcc attcaggctg cgcaactgtt  11340

gggaagggcg atcggtgcgg gcctcttcgc tattacgcca gctggcgaaa gggggatgtg  11400

ctgcaaggcg attaagttgg gtaacgccag ggttttccca gtcacgacgt tgtaaaacga  11460

cggccagtgc caagctttgt ttaaaatata acaaaattgt gatcccacaa aatgaagtgg  11520

ggcaaaatca aataattaat agtgtccgta aacttgttgg tcttcaactt tttgaggaac  11580

acgttggacg gcaaatccgt gactataaca caagttgatt taataatttt agccaacacg  11640

tcgggctgcg tgtttttgc cgacgcgtct gtgtacacgt tgattaactg gtcgattaaa  11700

ctgttgaaat aatttaattt ttggttcttc tttaaatctg tgatgaaatt ttttaaaata  11760

actttaaatt cttcattggt aaaaaatgcc acgttttgca acttgtgagg gtctaatatg  11820

aggtcaaact cagtaggagt tttatccaaa aaagaaaaca tgattacgtc tgtacacgaa  11880

cgcgtattaa cgcagagtgc aaagtataag agggttaaaa aatatatttt acgcaccata  11940

tacgcatcgg gttgatatcg ttaatatgga tcaatttgaa cagttgatta acgtgtctct  12000

gctcaagtct ttgatcaaaa cgcaaatcga cgaaaatgtg tcggacaata tcaagtcgat  12060

gagcgaaaaa ctaaaaaggc tagaatacga caatctcaca gacagcgttg agatatacgg  12120

tattcacgac agcaggctga ataataaaaa aattagaaac tattatttaa ccctagaaag  12180

ataatcatat tgtgacgtac gttaaagata atcatgcgta aaattgacgc atgtgtttta  12240

tcggtctgta tatcgaggtt tatttattaa tttgaataga tattaagttt tattatattt  12300

acacttacat actaataata aattcaacaa acaatttatt tatgtttatt tatttattaa  12360

aaaaaaacaa aaactcaaaa tttcttctat aaagtaacaa aactttttaaa cattctctct  12420

tttacaaaaa taaacttatt ttgtacttta aaaacagtca tgttgtatta taaaataagt  12480
```

-continued

```
aattagctta acttatacat aatagaaaca aattatactt attagtcagt cagaaacaac  12540
tttggcacat atcaatatta tgctctcgac aaataacttt tttgcatttt ttgcacgatg  12600
catttgcctt tcgccttatt ttagaggggc agtaagtaca gtaagtacgt tttttcatta  12660
ctggctcttc agtactgtca tctgatgtac caggcacttc atttggcaaa atattagaga  12720
tattatcgcg caaatatctc ttcaaagtag gagcttctaa acgcttacgc ataaacgatg  12780
acgtcaggct catgtaaagg tttctcataa attttttgcg actttggacc ttttctccct  12840
tgctactgac attatggctg tatataataa aagaatttat gcaggcaatg tttatcattc  12900
cgtacaataa tgccataggc cacctattcg tcttcctact gcaggtcatc acagaacaca  12960
tttggtctag cgtgtccact ccgcctttag tttgattata atacataacc atttgcggtt  13020
taccgggcgc ctcttaatta aggccccccc tcgagaccat ggtcgatcga caaacacgaa  13080
aatacattcc tggacagacc taggggtttg ctctttttc tttgcaggat ctggattcaa  13140
caaagaagga aaaatctacg gagtttggaa cctcatttat tgcacgaaga aacttagaga  13200
gaaagactga tgcctaataa agactcaagc tgattgcaaa aacaatataa agttgtacct  13260
tattgcggtg tcatcgtaaa accaagatgc ttaaaaggga ttaggcccac ttaaattact  13320
gcgaaaaatt ttatttacaa atttctcaca tgacttccag ataaactaat taactttgtg  13380
tgtcaaggtt gcttttccgg cagaaaagtc aatttgcaag tgatttaggt ttttttaatg  13440
actatctttg caattgaatt gggtactatt agatattgaa tataccaata ttgaggtata  13500
atacaaatac aacaacattt gacctcggca actatcagaa gtacatgtag gtcgggaaca  13560
ttagggaatt ctgcgcgata agttactaat tatgctaagc tatcgcagaa cctcattaag  13620
acttgagctg cagtgttttg caggtactta tcatatttac agtattaatg tatgcagtat  13680
tatattaatt ctaaataaga aagtcaggag aaggatattc aaaactgaag aattaatgta  13740
cattagtttt gtttattaga ttttcaatat tgcagcatag aatatgtgta agtagtggag  13800
agctaaacgc gcttttcaga acgttcatgc taattgctca tggatctcac aggaacaggt  13860
ggtggcggcc ctcggtgcgc tcgtactgct ccacgatggt gtagtcctcg ttgtgggagg  13920
tgatgtccag cttggcgtcc acgtagtagt agccgggcag ctgcacgggc ttcttggcca  13980
tgtagatgga cttgaactcc accaggtagt ggccgccgtc cttcagcttc agggccttgt  14040
gggtctcgcc cttcagcacg ccgtcgcggg ggtacaggcg ctcggtggag gcctcccagc  14100
ccatggtctt cttctgcatc acggggccgt cggaggggaa gttcacgccg atgaacttca  14160
ccttgtagat gaagcagccg tcctgcaggg aggagtcctg ggtcacggtc gccacgccgc  14220
cgtcctcgaa gttcatcacg cgctcccact tgaagccctc ggggaaggac agcttcttgt  14280
agtcggggat gtcggcgggg tgcttcacgt acaccttgga gccgtactgg aactgggggg  14340
acaggatgtc ccaggcgaag ggcagggggc cgcccttggt caccttcagc ttcacggtgt  14400
tgtggccctc gtaggggcgg ccctcgccct cgccctcgat ctcgaactcg tggccgttca  14460
cggtgccctc catgcgcacc ttgaagcgca tgaactcggt gatgacgttc tcggaggagg  14520
ccattctagc cattttggtt ctagatggca gttgtttatc tggaagggag atggaagtgc  14580
actcggttag ctcgatctgt cgattatata tgtaaagttt tatagctccc acctacatct  14640
caattcttta aattctacta ctttaatgac aacatagaaa actaatttgt gtctcaagaa  14700
aatatttaac tttttaagat attgaagaag tgaagtgaaa ctctattgtc catttgagca  14760
catttcagta aataaaacca tgaaaaattg ccaaaattgg tatattccat ttcctttga  14820
gtcatgctaa ttggttattc acttgaaact aaatcagtgc tctaaaaata tcggaaaaga  14880
```

```
atagttcata gaacttaatt taaacgtatc aaattaattg aaaatacgtt tcgttgcaat  14940

tactcttcac tttatattta gatattgaac tttcgaagac cgattagtga cttgtagaaa  15000

aatccatcaa acaatccgaa cttattaaaa agagttttaa tatccttagt cctcttggct  15060

ttttctgtaa taatccttgg atccttcgac attgaggtcg cactcacaca ccttttaggt  15120

caacgaaagg agaaaaattg gatagagtcg cacgttcgat tcctgttgac aactagattc  15180

aacaacaaat ggcacgccga tcggtctgtc ctgcctttat atctcggctc tccctcgaag  15240

cgatttgagt tggatgccag tgcggcactg agaaaaagat tgagcgaaag tgctgcggaa  15300

caatcaactc gaatcgatcc atataagcag ttttcagact tctggccgag catgtcagaa  15360

gtttggatgc ctcattgcac gaagacgact cattaatgcg cttcacaaaa aaaggaagcc  15420

acacaattaa atacttaata aagcatagaa tcatttatta agattaccaa taaattcaat  15480

aaacgaggga atttccaaac tgcgaaaata tgacatttta tatttttttc acattgttag  15540

taggtacaaa tcctagaaaa tggtctcata acatataaca gcttaaataa ctatgtagta  15600

gaagataaac tttatgttca attcagttca tatttaatcc tagaaatatt taattaattg  15660

acaatatatg atggaagtaa gctatcaatc ttaggaccct attcattatt tgtagggagt  15720

gccaggagag agaaagctct cgaaagataa gagaacgcca tagccgagtg attagcagag  15780

gtgcgtgata gtcggtgtat gggccaccta aacggcaatc agcactctcg agtggccaat  15840

tagccccatc tccgtcccca tctctgtccc aatcctgctg ccaatgggcg actgctgcgg  15900

cggacgactc attcggtgct gagagttcgg aaaatagaaa cggaccttag aaggaccgac  15960

gcaagacaat tggcatccgc ggcagggact gggagaatgg gacatttcaa cgggcacgca  16020

gcgaggcgaa tctaaaatag acgcgccaag cagagcggca cctataaatc aacatcaagg  16080

ttgatcgaga tatccaccca tctgcggccg ccatgcgtca attttacgca gactatcttt  16140

ctagggttaa tcagccc                                                16157
```

<210> SEQ ID NO 5
<211> LENGTH: 531
<212> TYPE: DNA
<213> ORGANISM: Drosophila melanogaster

<400> SEQUENCE: 5

```
gaaatcgatt gcggaaacca ttgcttagtt tttgattgac ctttgtttga aaacaaaata     60

tatgtataaa ggaattattt gaaagtacga gcggtttgtt gtcatattgg tgggattttt    120

ggctatttca ttttaattaa gttttttgaa tttaaatgtt tcatttagct acattcagaa    180

atattgtttt gaatttaaaa aatttacagt gtgaatgtct tgaatttttc aattggaaaa    240

aaaaggatga tggttgaagt atccgctttg tttattacag tagactggtc acactgccag    300

ctgctaaata atagaaaaca gtctgcgtgg acaaacattt aattaaaatg aatgtaagca    360

ctttttaacg aaatctttgg gaatatttcg ctcatcagca ttttatttga gcaggagtcc    420

gagtccccat cgacatacac acgctgaagc tgcaggactg gctgatcagc cgcagaattg    480

tgccaagaat gtgcagcagg agcttaggga gatccacagg aagattagca a             531
```

<210> SEQ ID NO 6
<211> LENGTH: 25
<212> TYPE: DNA
<213> ORGANISM: Artificial sequence
<220> FEATURE:
<223> OTHER INFORMATION: Synthetic

<400> SEQUENCE: 6
gccagtcctg cagcttcagc gtgtg 25

<210> SEQ ID NO 7
<211> LENGTH: 26
<212> TYPE: DNA
<213> ORGANISM: Artificial sequence
<220> FEATURE:
<223> OTHER INFORMATION: Synthetic

<400> SEQUENCE: 7
aaaggtatga tggttgaagt atccgc 26

<210> SEQ ID NO 8
<211> LENGTH: 26
<212> TYPE: DNA
<213> ORGANISM: Artificial sequence
<220> FEATURE:
<223> OTHER INFORMATION: Synthetic

<400> SEQUENCE: 8
ccttctttgt tgaatccaga tcctgc 26

<210> SEQ ID NO 9
<211> LENGTH: 23
<212> TYPE: DNA
<213> ORGANISM: Artificial sequence
<220> FEATURE:
<223> OTHER INFORMATION: Synthetic

<400> SEQUENCE: 9
gctcctgggc aacgtgctgg ttg 23

<210> SEQ ID NO 10
<211> LENGTH: 32
<212> TYPE: DNA
<213> ORGANISM: Artificial sequence
<220> FEATURE:
<223> OTHER INFORMATION: Synthetic

<400> SEQUENCE: 10
ggtggctagc ttgcgcttct tcttgggtgg gg 32

<210> SEQ ID NO 11
<211> LENGTH: 53
<212> TYPE: DNA
<213> ORGANISM: Artificial sequence
<220> FEATURE:
<223> OTHER INFORMATION: Synthetic

<400> SEQUENCE: 11
ggtgggcgcg cccaattgcc cgggcttttt aaccctagaa agatagtctg cgt 53

<210> SEQ ID NO 12
<211> LENGTH: 40
<212> TYPE: DNA
<213> ORGANISM: Artificial sequence
<220> FEATURE:
<223> OTHER INFORMATION: Synthetic

<400> SEQUENCE: 12
gcccaagctt gcggccgcgt cattttgact cacgcggtcg 40

<210> SEQ ID NO 13
<211> LENGTH: 29
<212> TYPE: DNA
<213> ORGANISM: Artificial sequence
<220> FEATURE:

<223> OTHER INFORMATION: Synthetic

<400> SEQUENCE: 13
gatttgattc agagttgatg ccattcatg 29

<210> SEQ ID NO 14
<211> LENGTH: 25
<212> TYPE: DNA
<213> ORGANISM: Artificial sequence
<220> FEATURE:
<223> OTHER INFORMATION: Synthetic

<400> SEQUENCE: 14
ccagacctcc accttcaagg tgacc 25

<210> SEQ ID NO 15
<211> LENGTH: 27
<212> TYPE: DNA
<213> ORGANISM: Artificial sequence
<220> FEATURE:
<223> OTHER INFORMATION: Synthetic

<400> SEQUENCE: 15
ttgtaggagg tgtggaactg gcatctg 27

<210> SEQ ID NO 16
<211> LENGTH: 25
<212> TYPE: DNA
<213> ORGANISM: Artificial sequence
<220> FEATURE:
<223> OTHER INFORMATION: Synthetic

<400> SEQUENCE: 16
caacaccgtg aagctgaagg tgacc 25

<210> SEQ ID NO 17
<211> LENGTH: 28
<212> TYPE: DNA
<213> ORGANISM: Artificial sequence
<220> FEATURE:
<223> OTHER INFORMATION: Synthetic

<400> SEQUENCE: 17
cttggccatg tagatggact tgaactcc 28

<210> SEQ ID NO 18
<211> LENGTH: 22
<212> TYPE: DNA
<213> ORGANISM: Artificial sequence
<220> FEATURE:
<223> OTHER INFORMATION: Synthetic

<400> SEQUENCE: 18
caagcaggcc atcaacctgt gc 22

<210> SEQ ID NO 19
<211> LENGTH: 24
<212> TYPE: DNA
<213> ORGANISM: Artificial sequence
<220> FEATURE:
<223> OTHER INFORMATION: Synthetic

<400> SEQUENCE: 19
gacttggcct tgtacacggt gtcg 24

<210> SEQ ID NO 20

```
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 20

wnwttaawnw                                                    10
```

The invention claimed is:

1. A transposable element comprising at least four inverted repeats, forming at least two pairs of opposing pairs of inverted repeats, the element comprising DNA for insertion into a host genome, the DNA being located between two pairs of opposing repeats such that excision by a transposase or transposases of said pairs, in situ, is effective to be able to leave said DNA integrated into the host genome, without the presence of said repeats flanking said DNA insertion.

2. The transposable element of claim 1, wherein the DNA for insertion into a host genome is a gene for expression in the host.

3. The transposable element of claim 1, wherein the DNA for insertion into a host genome is a promoter or enhancer sequence.

4. The transposable element of claim 1, wherein the DNA for insertion into a host genome is a stop codon or is sufficient to bring about an in frame stop codon.

5. The transposable element of claim 1, having four inverted repeats.

6. The transposable element of claim 1, wherein the inverted repeats are homologous to each other.

7. The transposable element of claim 1, wherein said pairs of homologous inverted repeats are heterologous to other pairs of inverted repeats.

8. The transposable element of claim 1, wherein one or more of the inverted repeats is a minimal non-terminal repeat.

9. The transposable element of claim 1, comprising at least one genetic marker.

10. The transposable element of claim 1, wherein the element comprises two external, opposed inverted repeats, one on each side of an inversion cassette, the cassette comprising:

the DNA for insertion into a host genome, two inverted cassette repeats and two inversion sites, the DNA for insertion into a host genome being flanked on either side by one of the inverted cassette repeats, each inverted cassette repeat being further flanked by an inversion site;

the cassette being capable of inversion within the transposed element in situ in the presence of a recombinase, such that following inversion, the two inverted cassette repeats flanking the DNA for insertion into a host genome each separately form a further pair of opposing inverted repeats with one of the external inverted repeats, the further pairs of opposing repeats being excisable by a transposase in situ to leave said DNA without flanking transposon-derived repeats in the host genome.

11. The transposable element of claim 10, wherein the inversion sites are recognised by inversion-inducing recombinase.

12. The transposable element of claim 11, wherein the inversion sites are recognised by the Flp/FRT or Cre/lox inversion systems.

13. The transposable element of claim 9, comprising at least one genetic marker associated with an identifiable step in the transposition/excision process.

14. The transposable element of claim 13, wherein the marker is associated with the DNA for insertion into a host genome.

15. The transposable element of 13, comprising as a terminal repeat, a repeat having a deletion of no more than 50%, or mutation or inversion that disables no more than 50% of the repeat.

16. The transposable element of claim 1, wherein the element is a class II transposable element.

17. The transposable element of claim 1, wherein the transposase is encoded within the transposon.

18. A method for transforming an insect comprising exposing replicative tissue of the insect to an element of claim 1 under conditions effective to incorporate the element into the genome thereof and, subsequently or simultaneously therewith, providing conditions suitable to excise said repeats from the genome, and selecting an organism, or tissue therefor, comprising the DNA intended for insertion lacking repeats in at least one orientation.

19. The method of claim 18, wherein the transformant insect is exposed to a source of active transposase.

20. The method of claim 19, wherein the source of active transposase comprises a helper plasmid or RNA encoding the transposase, or a transposase protein or integrated transposase source.

21. The transposable element of claim 9, wherein the marker is a conditional lethal.

22. The transposable element of claim 11, wherein the inversion sites are recognised by a directional recombinase, the recombinase-mediated inversion being essentially irreversible.

23. The transposable element of claim 22, wherein the inversion site is lox66 or lox71.

24. The transposable element of claim 1, which is effective to be able to leave said DNA integrated into the host genome without the presence of any transposon DNA.

25. The transposable element of claim 1, wherein the inverted repeats are repeats from Class II transposable elements.

26. The transposable element of claim 24, wherein the inverted repeats are piggyBac repeats.

27. The transposable elements of claim 24, wherein the inverted repeats are Hermes, hobo, Minos, or mariner repeats.

28. The method of claim 18, wherein the inverted repeats of the transposable element are repeats from Class II transposable elements.

29. The method of claim 28, wherein the inverted repeats are piggyBac repeats.

30. The method of claim 29, wherein the inverted repeats are Hermes, hobo, Minos, or mariner repeats.

* * * * *